United States Patent
Bhat et al.

(10) Patent No.: US 11,504,378 B2
(45) Date of Patent: Nov. 22, 2022

(54) PHARMACEUTICAL COMPOSITIONS COMPRISING (S)-2-(2,6-DIOXOPIPERIDIN-3-YL)-4-((2-FLUORO-4-((3-MORPHOLINOAZETIDIN-1-YL)METHYL)BENZYL)AMINO) ISOINDOLINE-1,3-DIONE AND METHODS OF USING THE SAME

(71) Applicant: Celgene Corporation, Summit, NJ (US)

(72) Inventors: Sreenivas S. Bhat, Kendall Park, NJ (US); Fabien Boulineau, Summit, NJ (US); Donna Carroll, Summit, NJ (US); Tracy Lee Gaebele, Green Brook, NJ (US); Yuchuan Gong, Summit, NJ (US); Isabel Minjung Hong, Summit, NJ (US); Zhengmao Li, Livingston, NJ (US); Ye Tian, Summit, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 17/075,447

(22) Filed: Oct. 20, 2020

(65) Prior Publication Data

US 2021/0113575 A1  Apr. 22, 2021

Related U.S. Application Data

(60) Provisional application No. 62/923,927, filed on Oct. 21, 2019.

(51) Int. Cl.
| | | |
|---|---|---|
| A61K 31/5377 | (2006.01) | |
| A61K 9/16 | (2006.01) | |
| A61K 9/48 | (2006.01) | |
| A61K 47/02 | (2006.01) | |
| A61K 47/12 | (2006.01) | |
| A61K 47/26 | (2006.01) | |
| A61K 47/32 | (2006.01) | |
| A61K 47/36 | (2006.01) | |
| A61K 47/38 | (2006.01) | |
| A61K 47/42 | (2017.01) | |

(52) U.S. Cl.
CPC ........ *A61K 31/5377* (2013.01); *A61K 9/1694* (2013.01); *A61K 9/485* (2013.01); *A61K 9/4816* (2013.01); *A61K 9/4858* (2013.01); *A61K 9/4866* (2013.01); *A61K 47/02* (2013.01); *A61K 47/12* (2013.01); *A61K 47/26* (2013.01); *A61K 47/32* (2013.01); *A61K 47/36* (2013.01); *A61K 47/38* (2013.01); *A61K 47/42* (2013.01)

(58) Field of Classification Search
CPC .... A61K 47/12; A61K 47/42; A61K 31/5377; A61K 9/4866; A61K 9/485; A61K 9/145; A61K 9/146; A61K 47/02; A61K 9/1682; A61K 47/32; A61K 47/36; A61K 47/38; A61K 9/4858; A61K 9/1694; A61K 47/26; A61K 9/14; A61K 9/1623; A61K 9/1652; A61K 9/4816
See application file for complete search history.

(56) References Cited

FOREIGN PATENT DOCUMENTS

| | | |
|---|---|---|
| WO | WO 2016/007854 A1 | 1/2016 |
| WO | WO 2019/209692 A1 | 10/2019 |
| WO | WO 2020/210418 A1 | 10/2020 |

OTHER PUBLICATIONS

Evans, Anthony E. "Principle of Radiopharmacology," Colombett, L.G. editor, CRC Press, pp. 11-13 and 24 (1979). (Year: 1979).*

* cited by examiner

*Primary Examiner* — Doan T Phan
(74) *Attorney, Agent, or Firm* — Jones Day

(57) ABSTRACT

Provided herein are pharmaceutical compositions (e.g., oral dosage formulations) comprising (S)-2-(2,6-dioxopiperidin-3-yl)-4-((2-fluoro-4-((3-morpholinoazetidin-1-yl)methyl) benzyl)amino)isoindoline-1,3-dione, or an enantiomer, mixture of enantiomers, tautomer, isotopolog, or pharmaceutically acceptable salt thereof, and a carrier or diluent. Also provided herein are methods of preparing and methods of using the pharmaceutical compositions.

42 Claims, 8 Drawing Sheets

Chemical stability (total impurity) of prototype formulations for up to 12 weeks

Chiral stability data of prototype formulations for up to 12 weeks

PHARMACEUTICAL COMPOSITIONS COMPRISING (S)-2-(2,6-DIOXOPIPERIDIN-3-YL)-4-((2-FLUORO-4-((3-MORPHOLINOAZETIDIN-1-YL)METHYL)BENZYL)AMINO) ISOINDOLINE-1,3-DIONE AND METHODS OF USING THE SAME

This application claims priority to U.S. Provisional Application No. 62/923,927, filed on Oct. 21, 2019, the entirety of which is incorporated herein by reference.

1. FIELD

Provided herein are pharmaceutical compositions comprising (S)-2-(2,6-dioxopiperidin-3-yl)-4-((2-fluoro-4-((3-morpholinoazetidin-1-yl)methyl)benzyl)amino)isoindoline-1,3-dione, or an enantiomer, mixture of enantiomers, tautomer, isotopolog, or pharmaceutically acceptable salt thereof, and a carrier or diluent. Methods of use of such pharmaceutical compositions for treating, preventing, and managing various disorders are also provided herein.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

Despite availability of a variety of chemotherapeutic agents, chemotherapy has many drawbacks. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Hematological malignancies are cancers that begin in blood-forming tissue, such as the bone marrow, or in the cells of the immune system. Examples of hematological malignancies are leukemia, lymphoma, and myeloma. More specific examples of hematological malignancies include but are not limited to acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), and myelodysplastic syndromes (MDS).

The variety of possible pharmaceutical compositions (e.g., oral dosage formulations comprising different excipients) creates potential diversity in physical and chemical properties for a given pharmaceutical compound. The discovery and selection of pharmaceutical compositions are of great importance in the development of an effective, stable and marketable pharmaceutical product.

3. SUMMARY

Provided herein are pharmaceutical compositions (e.g., oral dosage formulations) comprising Compound 1:

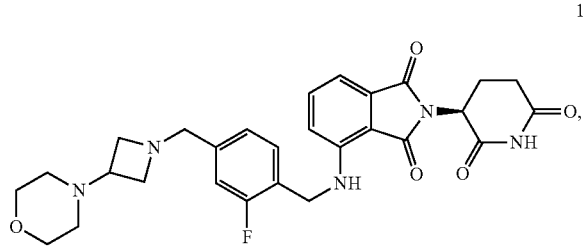 [SMILES: O=C1CC[C@H](N2C(=O)c3cccc(NCc4ccc(CN5CC(N6CCOCC6)C5)cc4F)c3C2=O)C(=O)N1]

or an enantiomer, mixture of enantiomers, tautomer, isotopolog, or pharmaceutically acceptable salt thereof, and a carrier or diluent. Compound 1 has the chemical name (S)-2-(2,6-dioxopiperidin-3-yl)-4-((2-fluoro-4-((3-morpholinoazetidin-1-yl)methyl)benzyl)amino)isoindoline-1,3-dione. Also provided herein are methods of preparing the pharmaceutical compositions. Compound 1, or an enantiomer, mixture of enantiomers, tautomer, isotopolog, or pharmaceutically acceptable salt thereof, is also collectively referred to as "Compound A".

In one embodiment, the carrier or diluent is mannitol, lactose, starch, cellulose, or a mixture thereof. In one embodiment, the carrier or diluent is mannitol, lactose, starch, cellulose, a mixture of mannitol and cellulose, or a mixture of mannitol and starch. In one embodiment, the carrier or diluent is a mixture of mannitol and starch. In some embodiments, the term "carrier" or "diluent" is used interchangeably with the term "binder".

The pharmaceutical compositions provided herein are useful formulations for use in animals or humans. Thus, embodiments herein encompass the use of these pharmaceutical compositions as a final drug product. Certain embodiments provide pharmaceutical compositions useful in making final dosage forms with improved properties, e.g., powder flow properties, compaction properties, tableting properties, stability properties, and excipient compatibility properties, among others, that are needed for manufacturing, processing, formulation and/or storage of final drug products.

Also provided are pharmaceutical compositions formulated for administration by an appropriate route and means containing effective concentrations of Compound A, for example Compound 1, provided herein. In one embodiment, the pharmaceutical compositions are oral dosage formulations. In one embodiment, the pharmaceutical compositions are immediate-release (IR) oral dosage formulations.

In one embodiment, the pharmaceutical compositions deliver amounts effective for the treatment of a hematological malignancy. In one embodiment, the pharmaceutical compositions deliver amounts effective for the prevention of a hematological malignancy. In one embodiment, the pharmaceutical compositions deliver amounts effective for the amelioration of a hematological malignancy.

In one embodiment, the hematological malignancy is acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), or myelodysplastic syndromes (MDS).

In one embodiment, the pharmaceutical compositions deliver amounts effective for the treatment of non-Hodgkin lymphoma. In one embodiment, the pharmaceutical compositions deliver amounts effective for the prevention of non-Hodgkin lymphoma. In one embodiment, the pharmaceutical compositions deliver amounts effective for the amelioration of non-Hodgkin lymphoma.

Also provided herein are methods of using a pharmaceutical composition provided herein, alone or in combination with rituximab, for treating, preventing or managing non-Hodgkin lymphoma (NHL). In one embodiment, the method is for treating NHL. In one embodiment, the method is for preventing NHL. In one embodiment, the method is for managing NHL.

In certain embodiments, the NHL is diffuse large B-cell lymphoma (DLBCL), follicular lymphoma (FL), mantle cell lymphoma (MCL), or primary central nervous system lymphoma (PCNSL).

Also provided herein are methods of using a pharmaceutical composition provided herein, alone or in combination with obinutuzumab, for treating, preventing or managing chronic lymphocytic leukemia (CLL). In one embodiment, the method is for treating CLL. In one embodiment, the method is for preventing CLL. In one embodiment, the method is for managing CLL.

Also provided herein are methods of using a pharmaceutical composition provided herein, alone or in combination with obinutuzumab, for treating, preventing or managing small lymphocytic lymphoma (SLL). In one embodiment, the method is for treating SLL. In one embodiment, the method is for preventing SLL. In one embodiment, the method is for managing SLL.

Also provided herein are pharmaceutical compositions provided herein for use in a method of treating a disease provided herein, wherein the method comprises administering to a patient a therapeutically effective amount of the pharmaceutical compositions.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

Further provided are processes for preparing the pharmaceutical compositions provided herein.

These and other aspects of the subject matter described herein will become evident upon reference to the following detailed description.

4. BRIEF DESCRIPTION OF THE DRAWINGS

FIG. 1A, FIG. 1B, and FIG. 1C show chemical stability (total impurity) of prototype formulations for up to 12 weeks at 40° C./75% RH without desiccant, at 40° C./75% RH with desiccant, and at 50° C./75% RH with desiccant, respectively.

FIG. 2A, FIG. 2B, and FIG. 2C show chiral stability data of prototype formulations for up to 12 weeks at 40° C./75% RH without desiccant, at 40° C./75% RH with desiccant, and at 50° C./75% RH with desiccant, respectively.

FIG. 3 provides process maps of wet granulation process.

FIG. 4 provides process maps of RC process.

Figure 7:
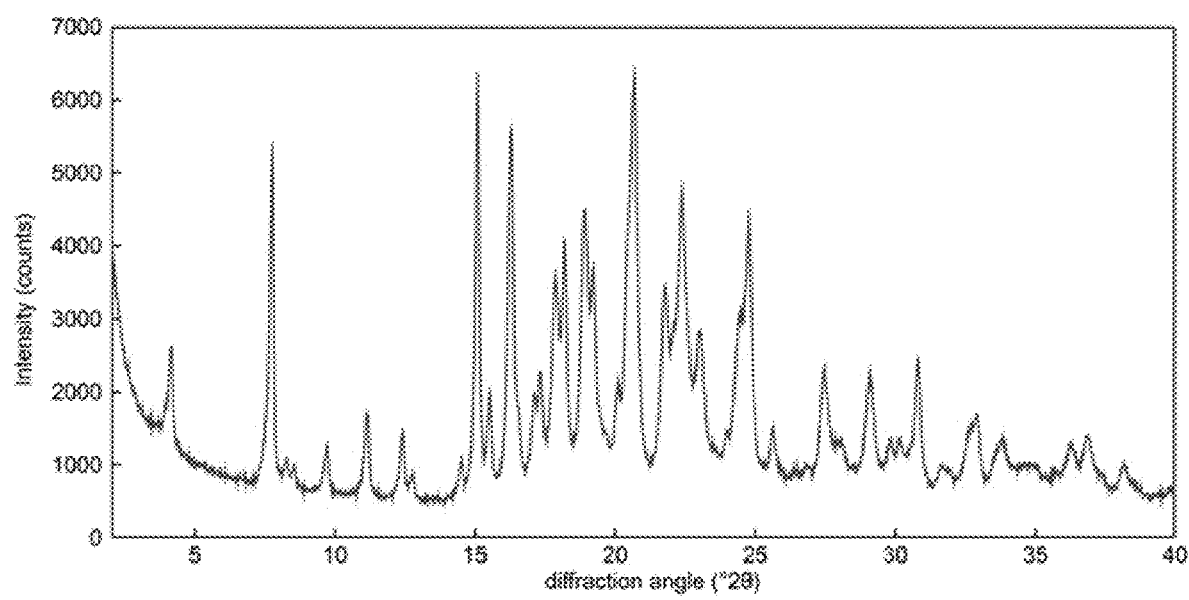

FIG. 7 provides a representative XRPD pattern of Form A of a hydrochloride salt of Compound 1.

5. DETAILED DESCRIPTION

5.1 Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, and in the specification and the accompanying claims, the indefinite articles "a" and "an" and the definite article "the" include plural as well as single references, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. As used herein, a tilde (i.e., "~") preceding a numerical value or range of values indicates "about" or "approximately."

Unless otherwise specified, the terms "X-ray powder diffraction", "powder X-ray diffraction", "PXRD", and "XRPD" are used interchangeably in this application.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ edition, 1843-1844 (1995).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, adipic, 4-aminosalicylic, ascorbic, aspartic, benzenesulfonic, benzoic, camphoric, camphorsulfonic, capric, caproic, caprylic, cinnamic, carbonic, citric, cyclamic, dihydrogenphosphoric, 2,5-dihydroxybenzoic (gentisic), 1,2 ethanedisulfonic, ethanesulfonic, fumaric, galactunoric, gluconic, glucuronic, glutamic, glutaric, glycolic, hippuric, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, 1,5-naphthalenedisulfonic, nicotinic, nitric, oxalic, pamoic, pantothenic, phosphoric, phthalic, propionic, pyroglutamic, salicylic, suberic, succinic, sulfuric, tartaric, toluenesulfonic acid, and the like (see, e.g., S. M. Berge et al., *J. Pharm. Sci.*, 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridinesulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy. In one embodiment, the disorder, disease or condition has been previously treated with one or more lines of therapy. In another embodiment, the disorder, disease or condition has been previously treated with one, two, three or four lines of therapy. In some embodiments, the disorder, disease or condition is a hematological malignancy.

In one embodiment, "relapsed" DLBCL may refer to DLBCL that has been previously treated with one or more lines of therapy. In one embodiment, the relapsed DLBCL is DLBCL that has been previously treated with one, two, three or four lines of therapy. In one embodiment, the relapsed DLBCL is DLBCL that has been previously treated with two or more lines of treatment.

In one embodiment, "relapsed" FL may refer to FL that has been previously treated with one or more lines of therapy. In one embodiment, the relapsed FL is FL that has been previously treated with one, two, three or four lines of therapy. In one embodiment, the relapsed FL is FL that has been previously treated with two or more lines of treatment.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen. In some embodiments, the disorder, disease or condition is a hematological malignancy.

In one embodiment, "relapsed or refractory" CLL/SLL may refer to CLL/SLL that has been previously treated with one or more lines of therapy. In one embodiment, the relapsed or refractory CLL/SLL is CLL/SLL that has been previously treated with one, two, three or four lines of therapy. In one embodiment, the relapsed or refractory CLL/SLL is CLL/SLL that has been previously treated with two or more lines of therapy. In one embodiment, the relapsed or refractory CLL/SLL is CLL/SLL that has been previously treated with a Bruton's tyrosine kinase (BTK) inhibitor. In one embodiment, the relapsed or refractory CLL/SLL is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In the context of a cancer, for example, a hematological malignancy, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates are computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR). In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of NHL may be assessed by the International Workshop Criteria for Malignant Lymphoma (see Cheson et al., *J. Clin. Oncol.* 2014, 32(27):3059-3068) and the Deauville Criteria for fluorodeoxyglucose-positron emission tomography (FDG-PET) scan interpretation (Itti et al., *Eur. J. Nucl. Med. Mol. Imaging*, 2013, 40(9):1312-20; Meignan et al., *Leuk Lymphoma*, 2014, 55(1):31-37) ("Lugano criteria"), using the response and end point definition shown in Tables 1-3.

TABLE 1

Criteria for Involvement of Site.

| Tissue Site | Clinical | FDG Avidity | Test | Positive Finding |
|---|---|---|---|---|
| Lymph nodes | Palpable | FDG-avid histologies | PET/CT | Increase FDG uptake |
| | | Nonavid disease | CT | Unexplained node enlargement |
| Spleen | Palpable | FDG-avid histologies | PET/CT | Diffuse uptake, solitary mass, miliary lesions, nodules |
| | | Nonavid disease | CT | >13 cm in vertical length, mass, nodules |
| Liver | Palpable | FDG-avid histologies | PET/CT | Diffuse uptake, mass |
| | | Nonavid disease | CT | Nodules |
| CNS | Signs, symptoms | N/A | CT | Mass lesion(s) |
| | | | MRI | Leptomeningeal infiltration, mass lesions |
| | | | CSF assessment | Cytology, flow cytometry |
| Other (eg, skin, lung, GI tract, bone, bone marrow) | Site dependent | N/A | PET/CT[a], biopsy | Lymphoma involvement |

CNS = central nervous system; CSF = cerebrospinal fluid; CT = computed tomography; FDG = fluorodeoxyglucose; GI = gastrointestinal; MRI = magnetic resonance imaging; PET = positron emission tomography; N/A = not applicable.

[a]PET/CT is adequate for determination of bone marrow involvement and can considered highly suggestive for involvement of other extralymphatic sites. Biopsy confirmation of those sites can be considered if necessary.

TABLE 2

Lugano Response Criteria for Non-Hodgkin Lymphoma.

| Response | Site | PET/CT (metabolic response) | CT (Radiologic response) |
|---|---|---|---|
| Complete response | Lymph nodes and extralymphatic sites | Score 1, 2, 3 with or without residual mass on 5-PS (Table 3) | All of the following: Target nodes/nodal masses must regress to ≤1.5 cm in LDi No extralymphatic sites of disease |
| | Non-measured lesion | N/A | Absent |
| | Organ enlargement | N/A | Regress to normal |
| | New Lesions | None | None |
| | Bone Marrow | No evidence of FDG-avid disease in marrow | Normal by morphology; if indeterminate, IHC negative[a] |
| Partial Response | Lymph nodes and extralymphatic sites | Score 4 or 5 on 5-PS with reduced uptake compared with baseline and residual mass(es) of any size At interim these findings suggest responding disease At end of treatment these findings may indicate residual disease | All of the following: ≥50% decrease in SPD of up to 6 target measureable nodes and extranodal sites When a lesion is too small to measure on CT, assign 5 mm × 5 mm as the default value When no longer visible, 0 mm × 0 mm For a node >5 mm × 5 mm, but smaller than normal, use actual measurement for calculation |

TABLE 2-continued

Lugano Response Criteria for Non-Hodgkin Lymphoma.

| Response | Site | PET/CT (metabolic response) | CT (Radiologic response) |
| --- | --- | --- | --- |
| | Non-measured lesion | N/A | Absent/normal, regressed, but no increase |
| | Organ enlargement | N/A | Spleen must have regressed by >50% in length beyond normal |
| | New Lesions | None | None |
| | Bone Marrow | Residual uptake higher than uptake in normal marrow but reduced compared with baseline. If persistent focal changes in the marrow in the context of nodal response, consider MRI or biopsy or interval scan | N/A |
| Stable Disease | Target nodes/nodal masses, extranodal lesions | Score 4 or 5 on 5-PS with no significant change in FDG uptake from baseline | <50% decrease from baseline of up to 6 dominant, measureable nodes and extranodal sites<br>No criteria for progressive disease are met |
| | Non-measured lesion | N/A | No increase consistent with progression |
| | Organ enlargement | N/A | No increase consistent with progression |
| | New Lesions | None | None |
| | Bone Marrow | No change from baseline | N/A |
| Progressive Disease | Lymph nodes and extralymphatic sites | Score 4 or 5 on 5-PS with an increase in intensity of uptake compared with baseline and/or<br>New FDG-avid foci consistent with lymphoma | At least one of the following:<br>PPD progression:<br>An individual node/lesion must be abnormal with:<br>LDi >1.5 cm and<br>Increase by ≥50% from PPD nadir and<br>An increase in LDi or SDi from nadir<br>0.5 cm for lesions ≤2 cm<br>1.0 cm for lesions >2 cm<br>In the setting of splenomegaly, splenic length must increase by >50% of the extent of its prior increase above baseline (eg, a 15 cm spleen must increase to >16 cm). If no splenomegaly, must increase by at least 2 cm from baseline must increase by at least 2 cm from baseline<br>New or recurrent splenomegaly |
| | Non-measured lesion | None | New or clear progression of preexisting nonmeasured lesions |
| | New Lesions | New FDG-avid foci consistent with lymphoma rather than another etiology (eg, infection, inflammation). If uncertain etiology, consider biopsy or interval scan | Regrowth of previously resolved lesions<br>A new node >1.5 cm in any axis<br>A new extranodal site >1.0 cm in any axis; if <1.0 cm in any axis, its presence must be unequivocal and must be attributable to lymphoma<br>Assessable disease of any size unequivocally attributable to lymphoma |
| | Bone Marrow | New of recurrent FDG-avid foci | New or recurrent involvement |

CMR = complete metabolic response; LDi = longest transverse diameter of a lesion; PPD = cross product of the LDi and perpendicular diameter; SDi = shortest axis perpendicular to the LDi; SPD = sum of the product of the perpendicular diameters for multiple lesions; N/A = not applicable.
[a] Required for CR if bone marrow involvement at baseline
[b] In Waldeyer's ring or extranodal sites with high physiologic uptake or with activation within spleen or marrow; (eg with chemotherapy or myeloid colony stimulating factors), uptake may be greater than normal mediastinum and/or liver. In this circumstance, CMR may be inferred if uptake at sites of initial involvement is no greater than surrounding normal tissue.
[c] FDG-avid lymphomas should have response assessed by PET-CT. Some diseases can typically be followed with CT alone (i.e., marginal zone lymphoma).
[d] PET should be done with contrast-enhanced diagnostic CT and can be done simultaneously or at separate procedures.

TABLE 3

PET Five Point Scale (5-PS).

| | |
|---|---|
| 1 | No uptake above background |
| 2 | Uptake ≤ mediastinum |
| 3 | Uptake > mediastinum but ≤ liver |
| 4 | Uptake moderately > liver |
| 5 | Uptake markedly higher than liver and/or new lesions |
| X | New areas of uptake unlikely to be related to lymphoma |

[a] The Deauville five-point scale (5PS) is an internationally recommended scale for clinical routine and clinical trials using FDG-PET/CT in the initial staging and assessment of treatment response in Hodgkin lymphoma (HL) and certain types of non-Hodgkin lymphomas (NHL).

In one embodiment, the treatment response of CLL/SLL may be assessed by the International Workshop on Chronic Lymphocytic Leukemia criteria (see Hallek, M, et al. iwCLL guidelines for diagnosis, indications for treatment, response assessment, and supportive management of CLL. *Blood*, 131(25), 2745-2760 (2018)) (Table 4).

TABLE 4

Response Definition after Treatment for Chronic Lymphocytic Leukemia Patients.

| Group | Parameter | CR | PR | PD | SD |
|---|---|---|---|---|---|
| A | Lymph nodes | None >1.5 cm | Decrease ≥50% (from the baseline)[a] | Increase ≥50% from baseline or from response | Change of −49% to +49% |
| | Liver and/or spleen size[b] | Spleen size, 13 cm; liver size normal | Decrease ≥50% (from the baseline) | Increase ≥50% from baseline or from response | Change of −49% to +49% |
| | Constitutional symptoms | None | Any | Any | Any |
| | Circulating lymphocyte count | Normal | Decrease ≥50% from baseline | Increase ≥50% over baseline | Change of −49% to +49% |
| B | Platelet count | ≥100 × 10$^9$/L | ≥100 × 10$^9$/L or increase ≥50% over baseline | Decrease of ≥50% from baseline secondary to CLL | Change of −49% to +49% |
| | Hemoglobin | ≥11.0 g/dL (untransfused and without erythropoietin) | ≥11.0 g/dL or increase ≥50% over baseline | Decrease of ≥2 g/dL from baseline secondary to CLL | Increase, 11.0 g/dL or <50% over baseline, or decrease <2 g/dL |
| | Marrow | Normocellular, no CLL cells, no B-lymphoid nodules | Presence of CLL cells, or of B-lymphoid nodules, or not done | Increase of CLL cells by ≥50% on successive biopsies | No change in marrow infiltrate |

CR = complete remission (all of the criteria have to be met); PD = progressive disease (at least 1 of the criteria of group A or group B has to be met); PR = partial remission (for a PR, at least 2 of the parameters of group A and 1 parameter of group B need to improve if previously abnormal; if only 1 parameter of both groups A and B is abnormal before therapy, only 1 needs to improve); SD = stable disease (all of the criteria have to be met; constitutional symptoms alone do not define PD).
[a]Sum of the products of 6 or fewer lymph nodes (as evaluated by CT scans and physical examination in clinical trials or by physical examination in general practice).
[b]Spleen size is considered normal if <13 cm. There is not firmly established international consensus of the size of a normal liver; therefore, liver size should be evaluated by imaging and manual palpation in clinical trials and be recorded according to the definition used in a study protocol.

In one embodiment, the treatment response of CLL/SLL may be assessed by the Eastern Cooperative Oncology Group (ECOG) performance status (Table 5).

TABLE 5

ECOG Performance Status.

| Grade | ECOG |
|---|---|
| 0 | Fully active, able to carry on all pre-disease performance without restriction. |
| 1 | Restricted in physically strenuous activity but ambulatory and able to carry out work of a light or sedentary nature, e.g., light house work, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |
| 5 | Dead. |

ECOG = Eastern Cooperative Oncology Group, Robert Comis, MD, Group Chair. Source: Oken M, et al. Toxicity and response criteria of the Eastern Cooperative Oncology Group. *Am J Clin Oncol*, 5(6): 649-655 (1982).

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, Mill (magnetic resonance imaging) of the brain and spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anti-cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

5.2 Pharmaceutical Compositions Comprising Compound 1

In certain embodiment, provided herein are pharmaceutical compositions (e.g., oral dosage formulations) comprising Compound 1:

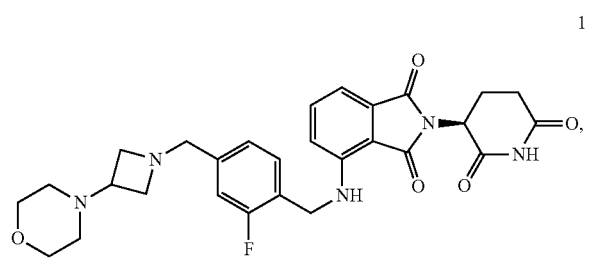 [SMILES: O=C1CC[C@H](N2C(=O)c3cccc(NCc4ccc(CN5CC(N6CCOCC6)C5)cc4F)c3C2=O)C(=O)N1]

or an enantiomer, mixture of enantiomers, tautomer, isotopolog, or pharmaceutically acceptable salt thereof, and a carrier or diluent. Compound 1, or an enantiomer, mixture of enantiomers, tautomer, isotopolog, or pharmaceutically acceptable salt thereof, is also collectively referred to as "Compound A".

In one embodiment, the carrier or diluent is mannitol, lactose, starch, cellulose, or a mixture thereof. In one embodiment, the carrier or diluent is mannitol, lactose, starch, cellulose, a mixture of mannitol and cellulose, or a mixture of mannitol and starch. In one embodiment, the carrier or diluent is a mixture of mannitol and starch. In some embodiments, the term "carrier" is used interchangeably with the term "binder".

In some embodiments, the pharmaceutical compositions provided herein are suitable for oral administration to a patient. In one embodiment, the pharmaceutical compositions provided herein exhibit advantageous physical and/or pharmacological properties. Such properties include, but are not limited to, ease of assay, content uniformity, flow properties for manufacture, dissolution and bioavailability, and stability. In one embodiment, the pharmaceutical compositions provided herein have a shelf life of at least about 6 months, at least about 12 months, at least about 18 months, at least about 24 months, at least about 30 months, or at least about 36 months without refrigeration. In certain embodiments, "without refrigeration" refers to a temperature at or above 20° C. In one embodiment, the pharmaceutical compositions provided herein are stored under refrigerated condition. In one embodiment, the pharmaceutical compositions provided herein have a shelf life of at least about 6 months, at least about 12 months, at least about 18 months, at least about 24 months, at least about 30 months, or at least about 36 months when stored under refrigerated condition. In one embodiment, the properties of the pharmaceutical compositions provided herein make them suitable for immediate-release (IR).

Pharmaceutical compositions provided herein can be formulated into suitable pharmaceutical formulations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel's Pharmaceutical Dosage Forms and Drug Delivery Systems, Tenth Edition 2013). In one embodiment, the pharmaceutical compositions provided herein are oral dosage forms. In one embodiment, the oral dosage unit form is a tablet. In one embodiment, the oral dosage unit form is a caplet. In one embodiment, the oral dosage unit form is a capsule. In one embodiment, the pharmaceutical compositions provided herein are immediate-release capsules.

Tablets, caplets, and capsules typically contain from about 50 mg to about 500 mg of the pharmaceutical composition (i.e., active ingredient and excipient(s)). Capsules can be of any size. Examples of standard sizes include #000, #00, #0, #1, #2, #3, #4, and #5. See, e.g., *Remington's Pharmaceutical Sciences*, page 1658-1659 (Alfonso Gennaro ed., Mack Publishing Company, Easton Pa., 18th ed., 1990), which is incorporated by reference. In some embodiments, capsules provided herein are of size #1 or larger, #2 or larger, #3 or larger, or #4 or larger.

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of non-Hodgkin lymphoma.

(a) Forms of Compound 1

Compound 1 has the chemical name (S)-2-(2,6-dioxopiperidin-3-yl)-4-((2-fluoro-4-((3-morpholinoazetidin-1-yl)methyl)benzyl)amino)isoindoline-1,3-dione. Methods of preparing Compound 1 are described in U.S. application Ser. No. 16/390,815, which is incorporated herein by reference in its entirety.

In one embodiment, Compound 1, or an enantiomer, mixture of enantiomers, tautomer, isotopolog, or pharmaceutically acceptable salt thereof, is provided in the pharmaceutical composition in a solid form. In one embodiment, the solid form is amorphous. In one embodiment, the solid form is crystalline. In one embodiment, the solid form is a hydrate. In one embodiment, the solid form is an anhydrate. In one embodiment, the solid form is a solvate. In one embodiment, the solid form is non-solvated.

The solid forms may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

In one embodiment, the pharmaceutical composition comprises free base of Compound 1. In one embodiment, the free base of Compound 1 is amorphous. In one embodiment, the free base of Compound 1 is crystalline. In one embodiment, the free base of Compound 1 is a mixture of one or more of amorphous form and crystalline forms.

In one embodiment, the pharmaceutical composition comprises a salt of Compound 1. In one embodiment, the salt is a hydrochloride salt, a fumarate salt, a tosylate salt, a maleate salt, or a besylate salt of Compound 1. In one embodiment, the salt of Compound 1 is amorphous. In one embodiment, the salt of Compound 1 is crystalline. In one embodiment, the salt of Compound 1 is a mixture of one or more of amorphous form and crystalline forms.

In one embodiment, the pharmaceutical composition comprises a hydrochloride salt of Compound 1. In one embodiment, the pharmaceutical composition comprises a fumarate salt of Compound 1. In one embodiment, the pharmaceutical composition comprises a tosylate salt of Compound 1. In one embodiment, the pharmaceutical composition comprises a maleate salt of Compound 1. In one embodiment, the pharmaceutical composition comprises a besylate salt of Compound 1.

In one embodiment, the pharmaceutical composition comprises Form A of a hydrochloride salt of Compound 1.

In one embodiment, Form A is a hydrate of a hydrochloride salt of Compound 1. In one embodiment, Form A is a channel hydrate of a hydrochloride salt of Compound 1.

A representative XRPD pattern of Form A of a hydrochloride salt of Compound 1 is provided in FIG. 7.

In one embodiment, the pharmaceutical composition provided herein comprises a hydrochloride salt of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, 26, 27, or all of the peaks located at approximately the following positions: 4.2, 7.8, 11.1, 12.4, 15.1, 15.5, 16.3, 17.1, 17.3, 17.9, 18.2, 18.9, 19.2, 20.1, 20.4, 20.7, 21.7, 22.4, 23.0, 24.4, 24.8, 25.7, 27.5, 28.1, 29.1, 29.8, 30.2, and 30.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises a hydrochloride salt of Compound 1, which is a solid form characterized by an XRPD pattern comprising peaks at approximately 15.1, 16.3, and 20.7° 2θ. In one embodiment, the XRPD pattern further comprises peaks at approximately 7.8 and 22.4° 2θ. In one embodiment, the XRPD pattern further comprises peaks at approximately 18.2, 18.9, and 24.8° 2θ. In one embodiment, the XRPD pattern comprises peaks at approximately 7.8, 15.1, 16.3, 17.9, 18.2, 18.9, 19.2, 20.4, 20.7, 21.7, 22.4, and 24.8° 2θ.

In one embodiment, the pharmaceutical composition provided herein comprises a hydrochloride salt of Compound 1, which is a solid form characterized by an XRPD pattern comprising peaks at approximately 4.2, 7.8, and 11.1° 2θ. In one embodiment, the XRPD pattern comprises peaks at approximately 4.2, 7.8, 11.1, 12.4, and 15.1° 2θ. In one embodiment, the XRPD pattern comprises peaks at approximately 4.2, 7.8, 11.1, 12.4, 15.1, 15.5, and 16.3° 2θ. In one embodiment, the XRPD pattern comprises peaks at approximately 4.2, 7.8, 11.1, 12.4, 15.1, 15.5, 16.3, 17.1, and 17.3° 2θ.

In one embodiment, the pharmaceutical composition provided herein comprises a hydrochloride salt of Compound 1, which is a solid form characterized by an XRPD pattern that matches the XRPD pattern presented in FIG. 7.

In one embodiment, the XRPD patterns are obtained using Cu Kα radiation.

(b) Mannitol-Starch Based Pharmaceutical Composition

In one embodiment, the carrier or diluent in the pharmaceutical composition provided herein is a mixture of mannitol and starch.

In one embodiment, the pharmaceutical composition further comprises a disintegrant, a glidant, a lubricant, or a mixture thereof.

In one embodiment, provided herein is a pharmaceutical composition, comprising: 1) Compound 1, or an enantiomer, mixture of enantiomers, tautomer, isotopolog, or pharmaceutically acceptable salt thereof, at an amount of from about 0.05 to about 2% w/w; 2) a mixture of mannitol and starch at an amount of from about 85 to about 99.7% w/w; 3) a disintegrant at an amount of from about 0 to about 6% w/w; 4) a glidant at an amount of from about 0 to about 2% w/w; and 5) a lubricant at an amount of from about 0 to about 10% w/w.

In one embodiment, Compound 1, or an enantiomer, mixture of enantiomers, tautomer, isotopolog, or pharmaceutically acceptable salt thereof, is a hydrochloride salt of Compound 1. In one embodiment, the hydrochloride salt of Compound 1 is a crystalline hydrochloride salt of Compound 1. In one embodiment, the hydrochloride salt of Compound 1 is characterized by an XRPD pattern comprising peaks at approximately 15.1, 16.3, and 20.7° 2θ.

In one embodiment, the amount of Compound 1, or an enantiomer, mixture of enantiomers, tautomer, isotopolog, or pharmaceutically acceptable salt thereof, is from about 0.05 to about 2% w/w (of the total weight of the pharmaceutical composition). In one embodiment, the amount is from about 0.07 to about 1.5% w/w. In one embodiment, the amount is from about 0.1 to about 1% w/w. In one embodiment, the amount is from about 0.14 to about 0.71% w/w. In one embodiment, the amount is from about 0.1 to about 0.2% w/w. In one embodiment, the amount is from about 0.6 to about 0.8% w/w.

In one embodiment, the amount of Compound 1, or an enantiomer, mixture of enantiomers, tautomer, isotopolog, or pharmaceutically acceptable salt thereof, is about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2% w/w. In one embodiment, the amount is about 0.14% w/w. In one embodiment, the amount is about 0.142% w/w. In one embodiment, the amount is about 0.71% w/w. In one embodiment, the amount is about 0.712% w/w.

In one embodiment, the starch is partially pregelatinized starch. In one embodiment, the starch is pregelatinized starch.

In one embodiment, the amount of the mixture of mannitol and starch is from about 85 to about 99.7% w/w (of the total weight of the pharmaceutical composition). In one embodiment, the amount of the mixture of starch and lactose is from about 87.5 to about 97.5% w/w. In one embodiment, the amount of the mixture of starch and lactose is from about 90 to about 95% w/w. In one embodiment, the amount of the mixture of starch and lactose is from about 91.5 to about 93% w/w. In one embodiment, the amount of the mixture of starch and lactose is from about 92 to about 93% w/w.

In one embodiment, the amount of the mixture of mannitol and starch is about 85, about 86, about 87, about 88, about 89, about 90, about 90.5, about 91, about 91.5, about 91.6, about 91.7, about 91.8, about 91.9, about 92, about 92.1, about 92.2, about 92.3, about 92.4, about 92.5, about 92.6, about 92.7, about 92.8, about 92.9, about 93, about 93.5, about 94, about 94.5, about 95, about 96, about 97, about 98, about 99, about 99.5, or about 99.7% w/w. In one embodiment, the amount of the mixture of mannitol and starch is about 91.9% w/w. In one embodiment, the amount of the mixture of mannitol and starch is about 92.3% w/w. In one embodiment, the amount of the mixture of mannitol and starch is about 92.9% w/w. In one embodiment, the amount of the mixture of mannitol and starch is about 91.86% w/w. In one embodiment, the amount of the mixture of mannitol and starch is about 92.29% w/w. In one embodiment, the amount of the mixture of mannitol and starch is about 92.86% w/w.

In one embodiment, the amount of the mannitol is from about 67 to about 77.7% w/w, and the amount of the starch is from about 18 to about 22% w/w. In one embodiment, the amount of the mannitol is from about 69 to about 76% w/w, and the amount of the starch is from about 18.5 to about 21.5% w/w. In one embodiment, the amount of the mannitol is from about 71 to about 74% w/w, and the amount of the starch is from about 19 to about 21% w/w. In one embodiment, wherein the amount of the mannitol is from about 71.5 to about 73% w/w, and the amount of the starch is about 20% w/w. In one embodiment, wherein the amount of the mannitol is from about 72 to about 73% w/w, and the amount of the starch is about 20% w/w.

In one embodiment, the amount of the mannitol is about 67, about 68, about 69, about 70, about 70.5, about 71, about 71.5, about 71.6, about 71.7, about 71.8, about 71.9, about 72, about 72.1, about 72.2, about 72.3, about 72.4, about 72.5, about 72.6, about 72.7, about 72.8, about 72.9, about 73, about 73.5, about 74, about 74.5, about 75, about 76, about 77, about 77.5, or about 77.7% w/w. In one embodiment, the amount of mannitol is about 71.9% w/w. In one embodiment, the amount of mannitol is about 72.3% w/w. In one embodiment, the amount of mannitol is about 72.9% w/w. In one embodiment, the amount of mannitol is about 71.86% w/w. In one embodiment, the amount of mannitol is about 72.29% w/w. In one embodiment, the amount of mannitol is about 72.86% w/w.

In one embodiment, the amount of the starch is about 18, about 18.5, about 19, about 19.5, about 20, about 20.5, about 21, about 21.5, or about 22% w/w. In one embodiment, the amount of the starch is about 20% w/w.

In one embodiment, the weight ratio of the starch to the mannitol is from about 1:3 to about 1:4. In one embodiment, the weight ratio of the starch to the mannitol is about 1:3, about 1:3.1, about 1:3.2, about 1:3.3, about 1:3.4, about 1:3.5, about 1:3.6, about 1:3.7, about 1:3.8, about 1:3.9, or about 1:4. In one embodiment, the weight ratio of the starch to the mannitol is about 1:3.6.

In one embodiment, the disintegrant is crospovidone.

In one embodiment, the amount of the disintegrant is from about 0 to about 6% w/w (of the total weight of the pharmaceutical composition). In one embodiment, the amount of the disintegrant is from about 1 to about 5% w/w. In one embodiment, the amount of the disintegrant is from about 2 to about 4% w/w.

In one embodiment, the amount of the disintegrant is about 0, about 1, about 2, about 3, about 4, about 5, or about 6% w/w. In one embodiment, the amount of the disintegrant is about 3% w/w. In one embodiment, the amount of the disintegrant is about 0% w/w (i.e., the pharmaceutical composition does not contain a disintegrant).

In one embodiment, the disintegrant is crospovidone at an amount of about 3% w/w.

In one embodiment, the glidant is silicon dioxide. In one embodiment, the glidant is colloidal silicon dioxide.

In one embodiment, the glidant is a hydrophilic glidant. In one embodiment, the glidant has a surface area of about 200 m$^2$/g. In one embodiment, the glidant is Aerosil 200.

In one embodiment, the amount of the glidant is from about 0 to about 2% w/w (of the total weight of the pharmaceutical composition). In one embodiment, the amount of the glidant is from about 0.25 to about 1.75% w/w. In one embodiment, the amount of the glidant is from about 0.5 to about 1.5% w/w. In one embodiment, the amount of the glidant is from about 0.75 to about 1.25% w/w.

In one embodiment, the amount of the glidant is about 0, about 0.1, about 0.2, about 0.25, about 0.3, about 0.4, about 0.5, about 0.55, about 0.6, about 0.65, about 0.7, about 0.75, about 0.8, about 0.85, about 0.9, about 0.95, about 1, about 1.05, about 1.1, about 1.15, about 1.2, about 1.25, about 1.3, about 1.35, about 1.4, about 1.45, about 1.5, about 1.6, about 1.7, about 1.75, about 1.8, about 1.9, or about 2% w/w. In one embodiment, the amount of the glidant is about 1% w/w. In one embodiment, the amount of the glidant is about 0% w/w (i.e., the pharmaceutical composition does not contain a glidant).

In one embodiment, the glidant is silicon dioxide at an amount of about 1% w/w.

In one embodiment, the lubricant is sodium stearyl fumarate, stearic acid, or magnesium stearate. In one embodiment, the lubricant is sodium stearyl fumarate. In one embodiment, the lubricant is stearic acid. In one embodiment, the lubricant is magnesium stearate.

In one embodiment, the amount of the lubricant is from about 0 to about 10% w/w (of the total weight of the pharmaceutical composition). In one embodiment, the amount of the lubricant is from about 1.5 to about 7.5% w/w. In one embodiment, the amount of the lubricant is from about 2 to about 6% w/w. In one embodiment, the amount of the lubricant is from about 2 to about 4% w/w. In one embodiment, the amount of the lubricant is from about 3 to about 5% w/w. In one embodiment, the amount of the lubricant is from about 4 to about 6% w/w.

In one embodiment, the amount of the lubricant is about 0, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10% w/w. In one embodiment, the amount of the lubricant is about 3% w/w. In one embodiment, the amount of the lubricant is about 5% w/w.

In one embodiment, the lubricant is sodium stearyl fumarate at an amount of about 3% w/w.

In one embodiment, the lubricant is stearic acid at an amount of about 5% w/w.

In one embodiment, provided herein is a pharmaceutical composition, comprising: 1) a hydrochloride salt of Compound 1 (e.g., Form A) at an amount of from about 0.1 to about 0.2% w/w; 2) mannitol at an amount of from about 71 to about 74% w/w and pregelatinized starch at an amount of from about 19 to about 21% w/w; 3) crospovidone at an amount of from about 2 to about 4% w/w; 4) silicon dioxide at an amount of from about 0.5 to about 1.5% w/w; and 5) sodium stearyl fumarate at an amount of from about 2 to about 4% w/w. In one embodiment, provided herein is a pharmaceutical composition, comprising: 1) a hydrochloride salt of Compound 1 (e.g., Form A) at an amount of about 0.14% w/w; 2) mannitol at an amount of about 72.86% w/w and pregelatinized starch at an amount of about 20% w/w; 3) crospovidone at an amount of about 3% w/w; 4) silicon dioxide at an amount of about 1% w/w; and 5) sodium stearyl fumarate at an amount of about 3% w/w. In one embodiment, the pharmaceutical composition has a total weight of about 75 mg. In one embodiment, the pharmaceutical composition is contained in a size 4 capsule.

In one embodiment, provided herein is a pharmaceutical composition, comprising: 1) a hydrochloride salt of Compound 1 (e.g., Form A) at an amount of from about 0.6 to about 0.8% w/w; 2) mannitol at an amount of from about 71 to about 74% w/w and pregelatinized starch at an amount of from about 19 to about 21% w/w; 3) crospovidone at an amount of from about 2 to about 4% w/w; 4) silicon dioxide at an amount of from about 0.5 to about 1.5% w/w; and 5) sodium stearyl fumarate at an amount of from about 2 to about 4% w/w. In one embodiment, provided herein is a pharmaceutical composition, comprising: 1) a hydrochloride salt of Compound 1 (e.g., Form A) at an amount of about 0.71% w/w; 2) mannitol at an amount of about 72.29% w/w and pregelatinized starch at an amount of about 20% w/w; 3) crospovidone at an amount of about 3% w/w; 4) silicon dioxide at an amount of about 1% w/w; and 5) sodium stearyl fumarate at an amount of about 3% w/w. In one embodiment, the pharmaceutical composition has a total weight of about 75 mg. In one embodiment, the pharmaceutical composition is contained in a size 4 capsule. In one embodiment, the pharmaceutical composition has a total weight of about 225 mg. In one embodiment, the pharmaceutical composition is contained in a size 1 capsule.

In one embodiment, provided herein is a pharmaceutical composition, comprising: 1) a hydrochloride salt of Compound 1 (e.g., Form A) at an amount of from about 0.1 to about 0.2% w/w; 2) mannitol at an amount of from about 71 to about 74% w/w and pregelatinized starch at an amount of from about 19 to about 21% w/w; 3) crospovidone at an amount of from about 2 to about 4% w/w; and 4) stearic acid at an amount of from about 4 to about 6% w/w. In one embodiment, provided herein is a pharmaceutical composition, comprising: 1) a hydrochloride salt of Compound 1 (e.g., Form A) at an amount of about 0.14% w/w; 2) mannitol at an amount of about 71.86% w/w and pregelatinized starch at an amount of about 20% w/w; 3) crospovidone at an amount of about 3% w/w; and 4) stearic acid at an amount of about 5% w/w.

In one embodiment, provided herein is a pharmaceutical composition, comprising: 1) a hydrochloride salt of Compound 1 (e.g., Form A) at an amount of from about 0.1 to about 0.2% w/w; 2) mannitol at an amount of from about 74 to about 77% w/w and pregelatinized starch at an amount of from about 19 to about 21% w/w; 3) crospovidone at an amount of from about 2 to about 4% w/w; and 4) magnesium stearate at an amount of from about 0.5 to about 1.5% w/w. In one embodiment, provided herein is a pharmaceutical composition, comprising: 1) a hydrochloride salt of Compound 1 (e.g., Form A) at an amount of about 0.14% w/w; 2) mannitol at an amount of about 75.86% w/w and pregelatinized starch at an amount of about 20% w/w; 3) crospovidone at an amount of about 3% w/w; and 4) magnesium stearate at an amount of about 1% w/w.

(c) Mannitol-Cellulose Based Pharmaceutical Composition

In one embodiment, the carrier or diluent in the pharmaceutical composition provided herein is a mixture of mannitol and cellulose. In one embodiment, the pharmaceutical composition further comprises a disintegrant, a glidant, a lubricant, or a mixture thereof.

In one embodiment, provided herein is a pharmaceutical composition, comprising: 1) Compound 1, or an enantiomer, mixture of enantiomers, tautomer, isotopolog, or pharmaceutically acceptable salt thereof, at an amount of from about 0.05 to about 2% w/w; 2) a mixture of mannitol and cellulose at an amount of from about 85 to about 99.7% w/w; 3) a disintegrant at an amount of from about 0 to about 6% w/w; and 4) a lubricant at an amount of from about 0 to about 10% w/w.

In one embodiment, provided herein is a pharmaceutical composition, comprising: 1) a hydrochloride salt of Compound 1 (e.g., Form A) at an amount of from about 0.1 to about 0.2% w/w; 2) mannitol at an amount of from about 72 to about 75% w/w and microcrystalline cellulose at an amount of from about 19 to about 21% w/w; 3) crospovidone at an amount of from about 2 to about 4% w/w; and 4) sodium stearyl fumarate at an amount of from about 2 to about 4% w/w. In one embodiment, provided herein is a pharmaceutical composition, comprising: 1) a hydrochloride salt of Compound 1 (e.g., Form A) at an amount of about 0.14% w/w; 2) mannitol at an amount of about 73.86% w/w and microcrystalline cellulose at an amount of about 20% w/w; 3) crospovidone at an amount of about 3% w/w; and 4) sodium stearyl fumarate at an amount of about 3% w/w.

In one embodiment, provided herein is a pharmaceutical composition, comprising: 1) a hydrochloride salt of Compound 1 (e.g., Form A) at an amount of from about 0.1 to about 0.2% w/w; 2) mannitol at an amount of from about 70 to about 73% w/w and microcrystalline cellulose at an amount of from about 19 to about 21% w/w; 3) crospovidone at an amount of from about 2 to about 4% w/w; and 4) stearic acid at an amount of from about 4 to about 6% w/w. In one embodiment, provided herein is a pharmaceutical composition, comprising: 1) a hydrochloride salt of Compound 1 (e.g., Form A) at an amount of about 0.14% w/w; 2) mannitol at an amount of about 71.86% w/w and microcrystalline cellulose at an amount of about 20% w/w; 3) crospovidone at an amount of about 3% w/w; and 4) stearic acid at an amount of about 5% w/w.

(d) Cellulose Based Pharmaceutical Composition

In one embodiment, the carrier or diluent in the pharmaceutical composition provided herein is cellulose. In one embodiment, the pharmaceutical composition further comprises a disintegrant, a glidant, a lubricant, or a mixture thereof.

In one embodiment, provided herein is a pharmaceutical composition, comprising: 1) Compound 1, or an enantiomer, mixture of enantiomers, tautomer, isotopolog, or pharmaceutically acceptable salt thereof, at an amount of from about 0.05 to about 2% w/w; 2) cellulose at an amount of from about 75 to about 95% w/w; 3) a disintegrant at an amount of from about 0 to about 20% w/w; and 4) a lubricant at an amount of from about 0 to about 10% w/w.

In one embodiment, provided herein is a pharmaceutical composition, comprising: 1) a hydrochloride salt of Compound 1 (e.g., Form A) at an amount of from about 0.1 to about 0.2% w/w; 2) microcrystalline cellulose at an amount of from about 82 to about 87% w/w; 3) crospovidone at an amount of from about 8 to about 12% w/w; and 4) stearic acid at an amount of from about 4 to about 6% w/w. In one embodiment, provided herein is a pharmaceutical composition, comprising: 1) a hydrochloride salt of Compound 1 (e.g., Form A) at an amount of about 0.14% w/w; 2) microcrystalline cellulose at an amount of about 84.86% w/w; 3) crospovidone at an amount of about 10% w/w; and 4) stearic acid at an amount of about w/w.

(e) Additional Embodiments of the Pharmaceutical Compositions

In one embodiment, the pharmaceutical compositions provided herein can optionally further comprises one or more additional excipient. The additional excipients include, but are not limited to, wetting agent, solubilizer, crystallization stabilizer, anti-adherent, and precipitation inhibitor.

In one embodiment, the pharmaceutical compositions provided herein are formulated into a capsule. In one embodiment, the capsule is an HPMC capsule.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

(f) Process for Making Dosage Forms

Pharmaceutical compositions (dosage forms) provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of hydroxypropyl methyl cellulose, calcium alginate, or gelatin.

In some embodiments, the active ingredients and excipients are directly blended and loaded into, for example, a capsule, or compressed directly into tablets.

In some embodiments, a dosage form or pharmaceutical composition provided herein is prepared by a wet granulation process. In one embodiment, the wet granulation process comprises the steps of: (i) mixing the active ingredient (e.g., Compound 1, or an enantiomer, mixture of enantiomers, tautomer, isotopolog, or pharmaceutically acceptable salt thereof) with a first portion of the excipient(s) (intragranular excipient) and water to form wet granules; (ii) drying and then milling (e.g., through a comil) the granules; and (iii) mixing the milled granules with the remaining excipient(s) (extragranular excipient) to form a final blend. In one embodiment, the process is followed by an encapsulation step.

In one embodiment, the intragranular excipient includes binder (e.g., starch) and disintegrant (e.g., crospovidone), and the extragranular excipient includes diluent (e.g., mannitol) and lubricant (e.g., stearic acid). In one embodiment, the intragranular/extragranular excipient ratio is no more than about 33:67. In one embodiment, the intragranular/extragranular excipient ratio is no more than about 23:77. In one embodiment, the intragranular/extragranular excipient ratio is about 23:77.

In one embodiment, the active ingredient is passed through a 60 mesh (250 μm) screen or a screen with smaller pore size, before step (i).

In one embodiment, the particle size of the milled granules (e.g., as measured by D50) matches (e.g., within ±10%, ±20%, or ±30%) the particle size of the major component of the extragranular excipient (e.g., a diluent, e.g., mannitol).

In some embodiments, a dosage form or pharmaceutical composition provided herein is prepared by a roller compaction process. In one embodiment, the roller compaction process comprises the steps of: (i) mixing the active ingredient (e.g., Compound 1, or an enantiomer, mixture of enantiomers, tautomer, isotopolog, or pharmaceutically acceptable salt thereof) with a first portion of the excipient(s) (intragranular excipient) to form an intragranular blend; (ii) passing the intragranular blend through a roller compactor to form dry granules; and (iii) mixing the dry granules with the remaining excipient(s) (extragranular excipient) to form a final blend. In one embodiment, step (i) includes pre-mixing the active ingredient with a small portion of binder (e.g., starch) and then mixing it with the remaining intragranular excipients. In one embodiment, the process is followed by an encapsulation step.

In one embodiment, the active ingredient is passed through a 60 mesh (250 μm) screen or a screen with smaller pore size, before step (i).

In one embodiment, the intragranular excipient includes binder (e.g., starch), diluent (e.g., mannitol), disintegrant (e.g., crospovidone), glidiant (e.g., silicon dioxide), and lubricant (e.g., sodium stearyl fumarate), and the extragranular excipient includes glidiant (e.g., silicon dioxide) and lubricant (e.g., sodium stearyl fumarate). In one embodiment, the intragranular/extragranular excipient ratio is no less than about 67:33. In one embodiment, the intragranular/extragranular excipient ratio is no less than about 98:2. In one embodiment, the intragranular/extragranular excipient ratio is about 98:2.

5.3 Methods of Use

In one embodiment, provided herein is a method of treating a hematological malignancy, which comprises administering to a patient a therapeutically effective amount of a pharmaceutical composition provided herein.

In one embodiment, provided herein is a method of preventing a hematological malignancy, which comprises administering to a patient a therapeutically effective amount of a pharmaceutical composition provided herein.

In one embodiment, provided herein is a method of managing a hematological malignancy, which comprises administering to a patient a therapeutically effective amount of a pharmaceutical composition provided herein.

In one embodiment, the hematological malignancy is leukemia.

In one embodiment, the hematological malignancy is acute myeloid leukemia. In one embodiment, the acute myeloid leukemia is B-cell acute myeloid leukemia.

In one embodiment, the hematological malignancy is acute lymphocytic leukemia.

In one embodiment, the hematological malignancy is chronic lymphocytic leukemia/small lymphocytic lymphoma.

In one embodiment, the hematological malignancy is myeloma.

In one embodiment, the hematological malignancy is multiple myeloma. In one embodiment, the multiple myeloma is plasma cell leukemia (PCL).

In one embodiment, the hematological malignancy is lymphoma.

In one embodiment, the hematological malignancy is non-Hodgkin's lymphoma.

In one embodiment, the hematological malignancy is diffuse large B-cell lymphoma.

In one embodiment, the hematological malignancy is T-cell lymphoma. In one embodiment, the T-cell lymphoma is anaplastic large cell lymphoma (ALCL). In one embodiment, the T-cell lymphoma is Sezary Syndrome.

In one embodiment, the hematological malignancy is Burkitt lymphoma.

In one embodiment, the hematological malignancy is marginal zone lymphoma. In one embodiment, the marginal zone lymphoma is splenic marginal zone lymphoma (SMZL).

In one embodiment, the hematological malignancy is Hodgkin's lymphoma.

In one embodiment, the hematological malignancy is myelodysplastic syndromes.

In one embodiment, the hematological malignancy is newly diagnosed. In one embodiment, the hematological malignancy is relapsed or refractory.

In one embodiment, the AML is newly diagnosed AML. In one embodiment, the AML is relapsed or refractory AML. In one embodiment, the B-cell AML is newly diagnosed B-cell AML. In one embodiment, the B-cell AML is relapsed or refractory B-cell AML.

In one embodiment, the ALL is newly diagnosed ALL. In one embodiment, the ALL is relapsed or refractory ALL.

In one embodiment, the MM is newly diagnosed MM. In one embodiment, the MM is relapsed or refractory MM. In one embodiment, the PCL is newly diagnosed PCL. In one embodiment, the PCL is relapsed or refractory PCL.

In one embodiment, the HL is newly diagnosed HL. In one embodiment, the HL is relapsed or refractory HL.

In one embodiment, the NHL is newly diagnosed NHL. In one embodiment, the NHL is relapsed or refractory NHL.

In one embodiment, the TCL is newly diagnosed TCL. In one embodiment, the TCL is relapsed or refractory TCL. In one embodiment, the ALCL is newly diagnosed ALCL. In one embodiment, the ALCL is relapsed or refractory ALCL. In one embodiment, the Sezary Syndrome is newly diagnosed Sezary Syndrome. In one embodiment, the Sezary Syndrome is relapsed or refractory Sezary Syndrome.

In one embodiment, the BL is newly diagnosed BL. In one embodiment, the BL is relapsed or refractory BL.

In one embodiment, the MZL is newly diagnosed MZL. In one embodiment, the MZL is relapsed or refractory MZL. In one embodiment, the SMZL is newly diagnosed SMZL. In one embodiment, the SMZL is relapsed or refractory SMZL.

In one embodiment, the MDS is newly diagnosed MDS. In one embodiment, the MDS is relapsed or refractory MDS.

In one embodiment, provided herein are methods for achieving a complete response, partial response, or stable disease in a patient, comprising administering to a patient having a hematological malignancy provided herein a therapeutically effective amount of a pharmaceutical composition provided herein. In one embodiment, provided herein are methods for achieving an increase in overall survival, progression-free survival, event-free survival, time to progression, or disease-free survival in a patient, comprising administering to a patient having a hematological malignancy provided herein a therapeutically effective amount of a therapeutically effective amount of a pharmaceutical composition provided herein. In one embodiment, provided herein are methods for achieving an increase in overall survival in a patient, comprising administering to a patient having a hematological malignancy provided herein a therapeutically effective amount of a therapeutically effective amount of a pharmaceutical composition provided herein. In one embodiment, provided herein are methods for achieving an increase in progression-free survival in a patient, comprising administering to a patient having a hematological malignancy provided herein a therapeutically effective amount of a pharmaceutical composition provided herein. In one embodiment, provided herein are methods for achieving an increase in event-free survival in a patient, comprising administering to a patient having a hematological malignancy provided herein a therapeutically effective amount of a therapeutically effective amount of a pharmaceutical composition provided herein. In one embodiment, provided herein are methods for achieving an increase in time to progression in a patient, comprising administering to a patient having a hematological malignancy provided herein a therapeutically effective amount of a therapeutically effective amount of a pharmaceutical composition provided herein. In one embodiment, provided herein are methods for achieving an increase in disease-free survival in a patient, comprising administering to a patient having a hematological malignancy provided herein a therapeutically effective amount of a therapeutically effective amount of a pharmaceutical composition provided herein. In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein is a method of treating AML, comprising administering to a subject in need thereof a therapeutically effective amount of a pharmaceutical composition provided herein. In one embodiment, the AML is B-cell AML.

In one embodiment, provided herein is a method of preventing AML, which comprises administering to a subject in need thereof a therapeutically effective amount of a pharmaceutical composition provided herein. In one embodiment, the AML is B-cell AML.

In one embodiment, provided herein is a method of managing AML, which comprises administering to a subject in need thereof a therapeutically effective amount of a pharmaceutical composition provided herein. In one embodiment, the AML is B-cell AML.

In one embodiment, provided herein is a method of treating ALL, comprising administering to a subject in need thereof a therapeutically effective amount of a pharmaceutical composition provided herein.

In one embodiment, provided herein is a method of preventing ALL, which comprises administering to a subject in need thereof a therapeutically effective amount of a pharmaceutical composition provided herein.

In one embodiment, provided herein is a method of managing ALL, which comprises administering to a subject in need thereof a therapeutically effective amount of a pharmaceutical composition provided herein.

In one embodiment, provided herein is a method of treating MM, comprising administering to a subject in need thereof a therapeutically effective amount of a pharmaceutical composition provided herein.

In one embodiment, provided herein is a method of preventing MM, which comprises administering to a subject in need thereof a therapeutically effective amount of a pharmaceutical composition provided herein.

In one embodiment, provided herein is a method of managing MM, which comprises administering to a subject in need thereof a therapeutically effective amount of a pharmaceutical composition provided herein.

In one embodiment, provided herein is a method of treating PCL, comprising administering to a subject in need thereof a therapeutically effective amount of a pharmaceutical composition provided herein.

In one embodiment, provided herein is a method of preventing PCL, which comprises administering to a subject in need thereof a therapeutically effective amount of a pharmaceutical composition provided herein.

In one embodiment, provided herein is a method of managing PCL, which comprises administering to a subject in need thereof a therapeutically effective amount of a pharmaceutical composition provided herein.

In one embodiment, provided herein is a method of treating TCL, comprising administering to a subject in need thereof a therapeutically effective amount of a pharmaceutical composition provided herein. In one embodiment, the TCL is ALCL. In one embodiment, the TCL is Sezary Syndrome.

In one embodiment, provided herein is a method of preventing TCL, which comprises administering to a subject in need thereof a therapeutically effective amount of a pharmaceutical composition provided herein. In one embodiment, the TCL is ALCL. In one embodiment, the TCL is Sezary Syndrome.

In one embodiment, provided herein is a method of managing TCL, which comprises administering to a subject in need thereof a therapeutically effective amount of a pharmaceutical composition provided herein. In one embodiment, the TCL is ALCL. In one embodiment, the TCL is Sezary Syndrome.

In one embodiment, provided herein is a method of treating BL, comprising administering to a subject in need thereof a therapeutically effective amount of a pharmaceutical composition provided herein.

In one embodiment, provided herein is a method of preventing BL, which comprises administering to a subject in need thereof a therapeutically effective amount of a pharmaceutical composition provided herein.

In one embodiment, provided herein is a method of managing BL, which comprises administering to a subject in need thereof a therapeutically effective amount of a pharmaceutical composition provided herein.

In one embodiment, provided herein is a method of treating HL, comprising administering to a subject in need thereof a therapeutically effective amount of a pharmaceutical composition provided herein.

In one embodiment, provided herein is a method of preventing HL, which comprises administering to a subject in need thereof a therapeutically effective amount of a pharmaceutical composition provided herein.

In one embodiment, provided herein is a method of managing HL, which comprises administering to a subject in need thereof a therapeutically effective amount of a pharmaceutical composition provided herein.

In one embodiment, provided herein is a method of treating MZL, comprising administering to a subject in need thereof a therapeutically effective amount of a pharmaceutical composition provided herein. In one embodiment, the MZL is SMZL.

In one embodiment, provided herein is a method of preventing MZL, which comprises administering to a subject in need thereof a therapeutically effective amount of a pharmaceutical composition provided herein. In one embodiment, the MZL is SMZL.

In one embodiment, provided herein is a method of managing MZL, which comprises administering to a subject in need thereof a therapeutically effective amount of a pharmaceutical composition provided herein. In one embodiment, the MZL is SMZL.

In one embodiment, provided herein is a method of treating MDS, comprising administering to a subject in need thereof a therapeutically effective amount of a pharmaceutical composition provided herein.

In one embodiment, provided herein is a method of preventing MDS, which comprises administering to a subject in need thereof a therapeutically effective amount of a pharmaceutical composition provided herein.

In one embodiment, provided herein is a method of managing MDS, which comprises administering to a subject in need thereof a therapeutically effective amount of a pharmaceutical composition provided herein.

In one embodiment, provided herein are methods of using a pharmaceutical composition provided herein, alone or in combination with rituximab, for treating, preventing or managing non-Hodgkin lymphoma (NHL).

In one embodiment, provided herein is a method of treating NHL, comprising administering to a subject in need thereof a therapeutically effective amount of a pharmaceutical composition provided herein.

In one embodiment, provided herein is a method of preventing NHL, which comprises administering to a subject in need thereof a therapeutically effective amount of a pharmaceutical composition provided herein.

In one embodiment, provided herein is a method of managing NHL, which comprises administering to a subject in need thereof a therapeutically effective amount of a pharmaceutical composition provided herein.

In one embodiment, the NHL is DLBCL. In one embodiment, the DLBCL is primary DLBCL. In one embodiment, the DLBCL is activated B-cell-like DLBCL (ABC-DLBCL). In one embodiment, the DLBCL is germinal center B-cell-like DLBCL (GCB-DLBCL). In one embodiment, the DLBCL is unclassified DLBCL. In one embodiment, the DLBCL is primary mediastinal B-cell type DLBCL (PMBL DLBCL). In one embodiment, the DLBCL is double-hit DLBCL (DHIT DLBCL), also referred to as cMyc/Bcl-2 mutant DLBCL. In one embodiment, the DLBCL is triple-hit DLBCL (THIT DLBCL) also referred to as cMyc/Bcl2/Bcl6 rearrangement DLBCL.

In one embodiment, the NHL is follicular lymphoma (FL).

In one embodiment, the NHL is mantle cell lymphoma (MCL).

In one embodiment, the NHL is primary central nervous system lymphoma (PCNSL).

In certain embodiments, the NHL is relapsed or refractory NHL. In one embodiment, the NHL is relapsed NHL. In one embodiment, the NHL is refractory NHL.

In certain embodiments, the NHL subject has radiological evidence of progression after achieving a complete response (CR). In certain embodiments, the NHL subject has achieved less than a CR to most recent systemic therapy containing regimen, and has radiological evidence of active disease or disease progression or recurrence in less than or equal to 12 months of prior stem cell transplantation (SCT).

In certain embodiments, the NHL subject has failed one or more lines of therapy and is not a candidate for other therapy. In certain embodiments, the subject has received at least one prior therapy and is not eligible for any therapy other than the methods of treatment described herein. In certain embodiments, the subject has relapsed after or progressed on standard anticancer therapy.

In certain embodiments, the subject has failed at least one prior therapy. In certain embodiments, the subject has failed at least two prior therapies.

In one embodiment, the NHL is relapsed or refractory DLBCL. In one embodiment, the DLBCL is relapsed DLBCL. In one embodiment, the DLBCL is refractory DLBCL. In one embodiment, the DLBCL is relapsed/refractory DLBCL. In one embodiment, the DLBCL is refractory to doxorubicin. In one embodiment, the DLBCL is resistant to doxorubicin. In one embodiment, the DLBCL is refractory to one or more of rituximab, cyclophosphamide, doxorubicin, vincristine, prednisone, etoposide, bendamustine, lenalidomide, gemcitabine, dexamethasone, ifosfamide, polatuxuab, or CAR-T.

In one embodiment, the DLBCL is treated with two or more prior lines of treatment.

In one embodiment, the DLBCL is transformed lymphoma. In another embodiment, the DLBCL is not otherwise specified (NOS) DLBCL.

In one embodiment, the NHL is relapsed or refractory FL. In one embodiment, the FL is relapsed FL. In one embodiment, the FL is refractory FL.

In one embodiment, the FL is treated with one or more prior lines of treatment. In one embodiment, the FL is treated with two or more prior lines of treatment.

In one embodiment, the NHL is relapsed or refractory MCL. In one embodiment, the MCL is relapsed MCL. In one embodiment, the MCL is refractory MCL.

In one embodiment, the MCL is treated with one or more prior lines of treatment. In one embodiment, the MCL is treated with two or more prior lines of treatment.

In one embodiment, the NHL is relapsed or refractory PCNSL. In one embodiment, the PCNSL is relapsed PCNSL. In one embodiment, the PCNSL is refractory PCNSL.

In certain embodiments, the NHL is newly diagnosed NHL. In certain embodiments, the NHL is newly diagnosed diffuse large B-cell lymphoma. In certain embodiments, the NHL is newly diagnosed follicular lymphoma. In certain embodiments, the NHL is newly diagnosed mantle cell lymphoma. In certain embodiments, the NHL is newly diagnosed primary central nervous system lymphoma.

In certain embodiments, the methods provided herein further comprise administering to the subject a therapeutically effective amount of rituximab.

In one embodiment, a first therapy provided herein (e.g., an agent such as a pharmaceutical composition provided herein) is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) to the administration of a second therapy (e.g., rituximab) to the subject.

In one embodiment, a first therapy provided herein (e.g., an agent such as a pharmaceutical composition provided herein) is administered concomitantly with the administration of a second therapy (e.g., rituximab) to the subject.

In one embodiment, a first therapy provided herein (e.g., an agent such as a pharmaceutical composition provided herein) is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., rituximab) to the subject.

In certain embodiments, rituximab is administered according to the locally approved label or Pharmacy manual for preparation, administration, and storage information. In certain embodiments, rituximab is administered intravenously. In certain embodiments, rituximab is administered subcutaneously. In certain embodiments, rituximab is administered via IV injection or IV infusion. In certain embodiments, rituximab is administered via IV infusion.

In certain embodiments, rituximab is administered at an amount according to the physician's decision. In certain embodiments, rituximab is administered once or twice daily. In certain embodiments, rituximab is administered in an amount of from about 50 to about 1000 mg/m$^2$, from about 100 to about 750 mg/m$^2$, from about 250 to about 500 mg/m$^2$, or from about 300 to about 400 mg/m$^2$. In certain embodiments, rituximab is administered in an amount of 375 mg/m$^2$ per day.

In one embodiment, provided herein is a method of treating DLBCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing DLBCL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing DLBCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating FL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing FL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing FL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating MCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing MCL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing MCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating PCNSL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing PCNSL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing PCNSL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating relapsed or refractory DLBCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing relapsed or refractory DLBCL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing relapsed or refractory DLBCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating relapsed or refractory FL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing relapsed or refractory FL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing relapsed or refractory FL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating relapsed or refractory MCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing relapsed or refractory MCL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing relapsed or refractory MCL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of treating relapsed or refractory PCNSL, which comprises administering to a subject in need thereof a therapeutically effective amount of a pharmaceutical composition provided herein. In one embodiment, the method further comprises administering to the subject a therapeutically effective amount of rituximab.

In one embodiment, provided herein is a method of preventing relapsed or refractory PCNSL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein is a method of managing relapsed or refractory PCNSL, which comprises administering to a subject in need thereof a therapeutically effective amount of a pharmaceutical composition provided herein. In one embodiment, the method further comprises administering to the subject a therapeutically effective amount of rituximab.

In another embodiment, provided herein are methods for achieving a complete response, partial response, or stable disease, as determined by the Lugano response criteria in a patient, comprising administering a therapeutically effective amount of a pharmaceutical composition provided herein, to patient having NHL. In another embodiment, provided herein are methods for achieving an increase in overall survival, progression-free survival, event-free survival, time to progression, or disease-free survival in a patient, comprising administering a therapeutically effective amount of a pharmaceutical composition provided herein, to patient having NHL. In another embodiment, provided herein are methods for achieving an increase in overall survival in a patient, comprising administering a therapeutically effective amount of a pharmaceutical composition provided herein, to patient having NHL. In another embodiment, provided herein are methods for achieving an increase in progression-free survival in a patient, comprising administering a therapeutically effective amount of a pharmaceutical composition provided herein, to patient having NHL. In another embodiment, provided herein are methods for achieving an increase in event-free survival in a patient, comprising administering a therapeutically effective amount of a pharmaceutical composition provided herein, to patient having NHL. In another embodiment, provided herein are methods for achieving an increase in time to progression in a patient, comprising administering a therapeutically effective amount of a pharmaceutical composition provided herein, to patient having NHL. In another embodiment, provided herein are methods for achieving an increase in disease-free survival in a patient, comprising administering a therapeutically effective amount of a pharmaceutical composition provided herein, to patient having NHL. In one embodiment, the methods further comprise administering to the subject a therapeutically effective amount of rituximab.

In one embodiment, provided herein are methods of using a pharmaceutical composition provided herein, alone or in combination with obinutuzumab, for treating, preventing or managing chronic lymphocytic leukemia/small lymphocytic lymphoma (CLL/SLL).

As used herein and unless otherwise indicated, "CLL/SLL" or "CLL and/or SLL" means CLL, or SLL, or CLL and SLL. In one embodiment, the methods provided herein are for treating, preventing or managing CLL. In one embodiment, the methods provided herein are for treating, preventing or managing SLL. In one embodiment, the methods provided herein are for treating, preventing or managing CLL and CLL.

In one embodiment, provided herein is a method of treating CLL/SLL, comprising administering to a subject in need thereof a therapeutically effective amount of a pharmaceutical composition provided herein.

In one embodiment, provided herein is a method of preventing CLL/SLL, which comprises administering to a subject in need thereof a therapeutically effective amount of a pharmaceutical composition provided herein.

In one embodiment, provided herein is a method of managing CLL/SLL, which comprises administering to a subject in need thereof a therapeutically effective amount of a pharmaceutical composition provided herein.

In one embodiment, the CLL/SLL subject has failed one or more lines of therapy. In one embodiment, the subject has failed at least one prior therapy. In one embodiment, the subject has failed at least two prior therapies. In one embodiment, the subject has been previously treated with a Bruton's tyrosine kinase (BTK) inhibitor. In one embodiment, the subject is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In one embodiment, the CLL/SLL is newly diagnosed CLL/SLL. In one embodiment, the CLL/SLL is relapsed or refractory CLL/SLL (R/R CLL/SLL).

In one embodiment, the CLL is characterized by mutated IGHV (Immunoglobulin Heavy Chain Gene). In one embodiment, the CLL is characterized by non-mutated IGHV.

In one embodiment, the CLL is characterized by one or more mutations in TP53 (Tumor Protein 53). In one embodiment, the CLL is characterized by wild type TP53.

In one embodiment, the CLL is characterized by one or more cytogenetic abnormalities, e.g., del(13q), del(11q), del(17p), tri12, t(6;17), del(11q22.3), t(11;14), del(18q), and t(14;19). In one embodiment, the CLL is characterized by del(17p).

In one embodiment, the CLL is characterized by Richter's Transformation (also known as Richter's Syndrome).

In one embodiment, the methods provided herein further comprise administering to the subject a therapeutically effective amount of obinutuzumab.

In one embodiment, a first therapy (e.g., an agent such as a pharmaceutical composition provided herein) provided herein is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks before) to the administration of a second therapy (e.g., obinutuzumab) to the subject.

In one embodiment, a first therapy (e.g., an agent such as a pharmaceutical composition provided herein) provided herein is administered concomitantly with the administration of a second therapy (e.g., obinutuzumab) to the subject.

In one embodiment, a first therapy (e.g., an agent such as a pharmaceutical composition provided herein) provided herein is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks after) the administration of a second therapy (e.g., obinutuzumab) to the subject.

In one embodiment, obinutuzumab is administered according to the locally approved label or Pharmacy manual for preparation, administration, and storage information. In one embodiment, obinutuzumab is administered intravenously. In one embodiment, obinutuzumab is administered subcutaneously. In one embodiment, obinutuzumab is administered via intravenous (IV) injection or IV infusion. In one embodiment, obinutuzumab is administered via IV injection. In one embodiment, obinutuzumab is administered via IV infusion.

In one embodiment, obinutuzumab is administered at an amount according to the physician's decision. In one embodiment, obinutuzumab is administered per day. In one embodiment, obinutuzumab is administered at a dose of from about 75 mg to about 1100 mg per day. In one embodiment, obinutuzumab is administered at a dose of from about 75 mg to about 125 mg per day, from about 800 mg to about 1000 mg per day, or from about 900 mg to about 1100 mg per day. In one embodiment, obinutuzumab is administered at a dose of about 100 mg per day. In one embodiment, obinutuzumab is administered at a dose of about 900 mg per day. In one embodiment, obinutuzumab is administered at a dose of about 1000 mg per day. In one embodiment, obinutuzumab is administered at a dose of about 100 mg on day 1 of a first 28-day cycle, about 900 mg on day 2 of the first 28-day cycle, and about 1000 mg on each of days 8 and 15 of the first 28-day cycle and day 1 of a second to a sixth 28-day cycles. In one embodiment, obinutuzumab is administered at a dose of about 1000 mg combined on day 1 and 2 of the first 28-day cycle, and about 1000 mg on each of days 8 and 15 of the first 28-day cycle and day 1 of a second to a sixth 28-day cycles. Obinutuzumab can be administered beyond six cycles. In one embodiment, obinutuzumab is administered in a first 28-day cycle as described herein, and is administered at about 1000 mg on day 1 of a second to a $12^{th}$ 28-day cycles. In one embodiment, obinutuzumab is administered in a first 28-day cycle as described herein, and is administered at about 1000 mg on day 1 of a second to a $24^{th}$ 28-day cycles. In one embodiment, obinutuzumab is administered in a first 28-day cycle as described herein, and is administered at about 1000 mg on day 1 of subsequent 28-day cycles until progression of disease.

In one embodiment, provided herein is a method of treating newly diagnosed CLL/SLL, which comprises administering to a subject in need thereof a therapeutically effective amount of a pharmaceutical composition provided herein. In one embodiment, the method further comprises administering to the subject a therapeutically effective amount of obinutuzumab.

In one embodiment, provided herein is a method of preventing newly diagnosed CLL/SLL, which comprises administering to a subject in need thereof a therapeutically effective amount of a pharmaceutical composition provided herein. In one embodiment, the method further comprises administering to the subject a therapeutically effective amount of obinutuzumab.

In another embodiment, provided herein is a method of managing newly diagnosed CLL/SLL, which comprises administering to a subject in need thereof a therapeutically effective amount of a pharmaceutical composition provided herein. In one embodiment, the method further comprises administering to the subject a therapeutically effective amount of obinutuzumab.

In one embodiment, provided herein is a method of treating relapsed or refractory CLL/SLL, which comprises administering to a subject in need thereof a therapeutically effective amount of a pharmaceutical composition provided herein. In one embodiment, the method further comprises administering to the subject a therapeutically effective amount of obinutuzumab.

In one embodiment, provided herein is a method of preventing relapsed or refractory CLL/SLL, which comprises administering to a subject in need thereof a therapeutically effective amount of a pharmaceutical composition provided herein. In one embodiment, the method further comprises administering to the subject a therapeutically effective amount of obinutuzumab.

In another embodiment, provided herein is a method of managing relapsed or refractory CLL/SLL, which comprises administering to a subject in need thereof a therapeutically effective amount of a pharmaceutical composition provided herein. In one embodiment, the method further comprises administering to the subject a therapeutically effective amount of obinutuzumab.

In another embodiment, provided herein are methods for achieving a complete response, partial response, or stable disease, as determined by the International Workshop on Chronic Lymphocytic Leukemia criteria in a patient, comprising administering a therapeutically effective amount of a pharmaceutical composition provided herein to patient having CLL/SLL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a pharmaceutical composition provided herein to patient having CLL/SLL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a pharmaceutical composition provided herein to patient having CLL/SLL. In another embodiment, provided herein are methods for achieving an increase in overall survival in a patient, comprising administering a therapeutically effective amount of a pharmaceutical composition provided herein to patient having CLL/SLL. In another embodiment, provided herein are methods for achieving an increase in progression-free survival in a patient, comprising administering a therapeutically effective amount of a pharmaceutical composition provided herein to patient having CLL/SLL. In another embodiment, provided herein are methods for achieving an increase in event-free survival in a patient, comprising administering a therapeutically effective amount of a pharmaceutical composition provided herein to patient having CLL/SLL. In another embodiment, provided herein are methods for achieving an increase in time to progression in a patient, comprising administering a therapeutically effective amount of a pharmaceutical composition provided herein to patient having CLL/SLL. In another embodiment, provided herein are methods for achieving an increase in disease-free survival in a patient, comprising administering a therapeutically effective amount of a pharmaceutical composition provided herein to patient having CLL/SLL. In one embodiment, the methods further comprise administering to the subject a therapeutically effective amount of obinutuzumab.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

Also provided herein is a pharmaceutical composition provided herein for use in a method of treating a disease provided herein, wherein the method comprises administering to a patient a therapeutically effective amount of the pharmaceutical composition provided herein.

5.4 Routes of Administration

A pharmaceutical composition provided herein can be administered orally. In one embodiment, when administered orally, a pharmaceutical composition provided herein is administered with a meal and water. In another embodiment, the pharmaceutical composition provided herein is dispersed in water or juice (e.g., apple juice or orange juice) and administered orally as a solution or a suspension.

A pharmaceutical composition provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry.

Depending on the state of the disease to be treated and the subject's condition, a pharmaceutical composition provided herein, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A pharmaceutical composition provided herein, may be formulated, alone or together, in suitable dosage unit with pharmaceutically acceptable excipients, carriers, adjuvants and vehicles, appropriate for each route of administration.

In one embodiment, a pharmaceutical composition provided herein is administered orally. In another embodiment, a pharmaceutical composition provided herein is administered parenterally. In yet another embodiment, a pharmaceutical composition provided herein is administered intravenously.

A pharmaceutical composition provided herein can be delivered as a single dose such as, e.g., a single bolus injection, or oral capsules, tablets or pills; or over time, such as, e.g., continuous infusion over time or divided bolus doses over time. The pharmaceutical composition provided herein can be administered repeatedly if necessary, for example, until the patient experiences stable disease or regression, or until the patient experiences disease progression or unacceptable toxicity.

A pharmaceutical composition provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as a pharmaceutical composition provided herein, is administered once or more than once each day, for example, for a period of time. The term "continuous" is intended to mean that a therapeutic compound, such as a pharmaceutical composition provided herein, is administered daily for an uninterrupted period of at least 7 days to 52 weeks. The term "intermittent" or "intermittently" as used herein is intended to mean stopping and starting at either regular or irregular intervals. For example, intermittent administration of a pharmaceutical composition provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as a pharmaceutical composition provided herein, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a pharmaceutical composition provided herein is administered once a day. In another embodiment, a pharmaceutical composition provided herein is administered twice a day. In yet another embodiment, a pharmaceutical composition provided herein is administered three times a day. In still another embodiment, a pharmaceutical composition provided herein is administered four times a day.

In certain embodiments, the methods provided herein include an administration of a therapeutically effective amount of a pharmaceutical composition provided herein in one or more 7-day treatment cycles. In another embodiment, the methods provided herein include an administration of a therapeutically effective amount of a pharmaceutical composition provided herein on days 1 to 5 of a 7-day cycle. In another embodiment, the methods provided herein include an administration of a therapeutically effective amount of a pharmaceutical composition provided herein on days 1 to 3 of a 7-day cycle.

In certain embodiments, the methods provided herein include an administration of a therapeutically effective amount of a pharmaceutical composition provided herein in one or more 14-day treatment cycles. In another embodiment, the methods provided herein include an administration of a therapeutically effective amount of a pharmaceutical composition provided herein on days 1 to 7 of a 14-day cycle. In another embodiment, the methods provided herein include an administration of a therapeutically effective amount of a pharmaceutical composition provided herein on days 1 to 10 of a 14-day cycle.

In certain embodiments, the methods provided herein include an administration of a therapeutically effective amount of a pharmaceutical composition provided herein in one or more 28-day treatment cycles. In another embodiment, the methods provided herein include an administration of a therapeutically effective amount of a pharmaceutical composition provided herein on days 1 to 21 of a 28-day cycle. In another embodiment, the methods provided herein include an administration of a therapeutically effective amount of a pharmaceutical composition provided herein on days 1 to 5, days 8 to 12, days 15 to 19, and days 22 to 26 of a 28-day cycle. In another embodiment, the methods provided herein include an administration of a therapeutically effective amount of a pharmaceutical composition provided herein on days 1 to 10 and days 15 to 24 of a 28-day cycle.

In one embodiment, a pharmaceutical composition provided herein is administered once daily for 5 days followed by 2 days of rest. In one embodiment, a pharmaceutical composition provided herein is administered once daily for 3 days followed by 4 days of rest. In one embodiment, a pharmaceutical composition provided herein is administered once daily for 7 days followed by 7 days of rest. In one embodiment, a pharmaceutical composition provided herein is administered once daily for 10 days followed by 4 days of rest. In one embodiment, a pharmaceutical composition provided herein is administered once daily for 21 days followed by 7 days of rest.

In certain embodiments, the treatment includes an administration of a therapeutically effective amount of rituximab in one or more treatment cycles. In one embodiment, rituximab is administered once every 7 days. In one embodiment, rituximab is administered once every 4 weeks. In one embodiment, rituximab is administered once every 8 weeks. In one embodiment, rituximab is administered at days 1, 8, 15, and 22 of the first 28-day cycle, administered at day 1 of the second to the sixth 28-day cycles, and then administered once every 8 weeks.

In one embodiment, the treatment includes an administration of a therapeutically effective amount of obinutuzumab in one or more treatment cycles. In one embodiment, obinutuzumab is administered twice every 7 days. In one embodiment, obinutuzumab is administered once every week. In one embodiment, obinutuzumab is administered once every 4 weeks. In one embodiment, obinutuzumab is administered on days 1, 2, 8, and 15 of the first 28-day cycle, and administered on day 1 of the second to the sixth 28-day cycles. In one embodiment, obinutuzumab is administered on day 1 of a second to a $12^{th}$ 28-day cycles. In one embodiment, obinutuzumab is administered on day 1 of a second to a $24^{th}$ 28-day cycles. In one embodiment, obinutuzumab is administered on day 1 of subsequent 28-day cycles until progression of disease.

In one embodiment, obinutuzumab is administered at a dose of about 100 mg on day 1 of the first 28-day cycle, about 900 mg on day 2 of the first 28-day cycle, and about 1000 mg on each of days 8 and 15 of the first 28-day cycle. In one embodiment, obinutuzumab is administered at a dose of about 1000 mg combined on day 1 and 2 of the first 28-day cycle, and about 1000 mg on each of days 8 and 15 of the first 28-day cycle. In one embodiment, obinutuzumab is administered at a dose of about 1000 mg on day 1 of the second to the sixth 28-day cycles. In one embodiment, obinutuzumab is administered at about 1000 mg on day 1 of a second to a $12^{th}$ 28-day cycles. In one embodiment, obinutuzumab is administered at about 1000 mg on day 1 of a second to a $24^{th}$ 28-day cycles. In one embodiment, obinutuzumab is administered at about 1000 mg on day 1 of subsequent 28-day cycles until progression of disease.

Any treatment cycle described herein can be repeated for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of a pharmaceutical composition provided herein and/or rituximab is administered for 1 to 13 cycles of 28 days (e.g., about 1 year). In some embodiments, a therapeutically effective amount of a pharmaceutical composition provided herein and/or rituximab is administered for 1 to 24 cycles of 28 days (e.g., about 2 years). In some embodiments, a therapeutically effective amount of a pharmaceutical composition provided herein and/or obinutuzumab is administered for 1 to 13 cycles of 28 days (e.g., about 1 year). In some embodiments, a therapeutically effective amount of a pharmaceutical composition provided herein and/or obinutuzumab is administered for 1 to 24 cycles of 28 days (e.g., about 2 years). In certain instances, the cycling therapy is not limited to the number of cycles, and the therapy is continued until disease progression. Cycles can in certain instances include varying the duration of administration periods and/or rest periods described herein.

6. EXAMPLES

Certain embodiments of the invention are illustrated by the following non-limiting examples.
Abbreviations used:

| | |
|---|---|
| DCM | Dichloromethane |
| DIEA | N,N-Diisopropylethylamine |
| DMSO | Dimethylsulfoxide |
| ESI | Electrospray ionization |
| EtOAc | Ethyl acetate |
| LCMS | Liquid chromatography mass spectrometry |
| MeOH | Methanol |
| MS | Mass spectrometry |
| NMP | N-Methylpyrrolidone |
| NMR | Nuclear magnetic resonance |

6.1 Synthesis of (S)-2-(2,6-dioxopiperidin-3-yl)-4-((2-fluoro-4-((3-morpholinoazetidin-1-yl)methyl)benzyl)amino)isoindoline-1,3-dione (Compound 1)

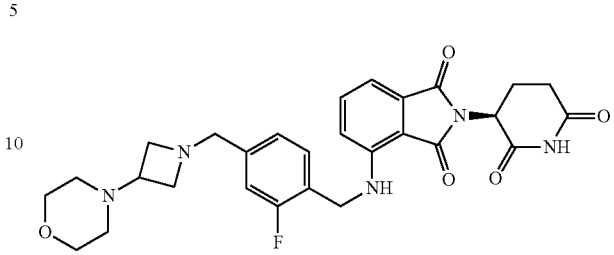

(S)-2-(2,6-Dioxopiperidin-3-yl)-4-((2-fluoro-4-(hydroxymethyl)benzyl)amino)isoindoline-1,3-dione: A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1, 3-dione as a yellow solid (4.23 g, 56%). LCMS (ESI) m/z 411.8 $[M+H]^+$.

(S)-4-((4-(Chloromethyl)-2-fluorobenzyl)amino)-2-(2,6-dioxopiperidin-3-yl)isoindoline-1,3-dione: A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to $H_2O$ (60 mL) cooled to 0° C. with vigorous mixing. The resulting suspension was filtered and the collected solid was washed with $H_2O$ and $Et_2O$. The solid was dissolved in EtOAc and the solution dried with $MgSO_4$, filtered and concentrated to provide (S)-4-((4-(chloromethyl)-2-fluorobenzyl)amino)-2-(2,6-dioxopiperidin-3-yl)isoindoline-1, 3-dione as a yellow solid (0.600 g, 79%). LCMS (ESI) m/z 430.0 $[M+H]^+$.

(S)-2-(2,6-Dioxopiperidin-3-yl)-4-((2-fluoro-4-((3-morpholinoazetidin-1-yl)methyl)benzyl)amino)isoindoline-1,3-dione: To a solution of (S)-4-((4-(chloromethyl)-2-fluorobenzyl)amino)-2-(2,6-dioxopiperidin-3-yl)isoindoline-1, 3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 $[M+H]^+$.

6.2 Cell-Based Assays Using Compound 1

The following are examples of cell-based assays that can be used to determine the anti-proliferative activity and apoptotic effect of Compound 1 using exemplary non-Hodgkin lymphoma (NHL) cell lines.

Cell Proliferation and Viability Assay Using SU-DHL-4 Cell Line: The following exemplary assay uses a DLBCL cell line, for example, the SU-DHL-4 cell line (Deutsche Sammlung von Mikroorganismen and Zellkulturen GmbH [DSMZ]: catalogue number ACC-495) at 120 hours post-treatment. The seeding density for SU-DHL-4 can be optimized to ensure assay linearity in 1536-well plates.

Increasing concentrations (0.5 nM to 10 μM) of Compound 1 were each spotted in a 20-point dilution fashion (unevenly spaced data points) via an acoustic dispenser (EDC ATS-100) into an empty 1536-well plate. The DMSO concentration was kept constant for a final assay concentration of 0.1% DMSO. Prior to testing, SU-DHL-4 cells were grown in RPMI-1640 (Roswell Park Memorial Institute-1640) medium with 10% FBS (fetal bovine serum: HyClone) and expanded in culture flasks to provide sufficient amounts of starting material. Cells were then diluted to 500 cells per well in a 5 μL volume, and added directly to the compound-spotted 1536-well plates. Cells were allowed to grow for 120 hours in 5% $CO_2$ at 37° C. At the time when exposure of cells to compound began (to), initial viable cell number was assessed via Cell Titer-Gb® Luminescent Cell Viability Assay at a 1 vol: 2 vol ratio according to manufacturer's instructions (Promega Corporation, Madison, Wis.) by quantifying the level of luminescence generated by adenosine-5'-triphosphate (ATP) present in viable cells. After 120 hours, cell viability of the treated cells was assessed via Cell Titer-Gb® and read for luminescence. All growth inhibition curves were processed and evaluated using Activity Base (IDBS, Alameda, Calif.). Cell viability $IC_{50}$ values were calculated using a four parameter logistic model (sigmoidal dose-response model):

$$y=(A+((B-A)/(1+((C/x)\hat{}D))))$$

wherein:
$A=Y_{Min}$
$B=Y_{Max}$
$C=EC_{50}$
D=Hill slope
$IC_{50}$=the concentration of the compound when Y=50% of DMSO control
Y=cell viability measured as luminescence unit, and
x=concentration of compound.

Compound 1 was found to have activity in SU-DHL-4 cell proliferation assay with an $IC_{50}$<0.2 μM.

Cell Proliferation and Viability Assay Using Hematological Cell Lines: The following exemplary anti-proliferative assay uses exemplary hematological cell lines in the following. The in vitro growth inhibitory activity of Compound 1 described herein was evaluated using a 384-well flow cytometry assay.

TABLE 6

| Hematological Cell Lines | | | |
|---|---|---|---|
| Cell Line | Tumor type | Tumor subtype | Culture conditions |
| ULA | DLBCL | not specified | RPMI + 10% FBS, 1X NEAA, 2 mM L-glutamine |
| SU-DHL-5 | DLBCL | not specified | |
| OCI-LY18 | DLBCL | not specified | |
| TMD8 | DLBCL | ABC | |
| SU-DHL-2 | DLBCL | ABC | |
| Farage | DLBCL | PMBL | |
| SU-DHL-10 | DLBCL | GCB | |
| NU-DHL-1 | DLBCL | GCB | |
| VAL | DLBCL | not specified | |
| WILL-2 | DLBCL | not specified | |
| SU-DHL-6 | DLBCL | GCB | |
| KARPAS-422 | DLBCL | GCB | |
| NU-DUL-1 | DLBCL | ABC | |
| KARPAS-1106P | DLBCL | PMBL | |
| OCI-LY1 | DLBCL | GCB | |
| SU-DHL-1 | DLBCL | not specified | |
| WSU-DLCL2 | DLBCL | GCB | |
| STR428 | DLBCL | not specified | |
| U-2946 | DLBCL | not specified | |
| U-2940 | DLBCL | PMBL | |
| OCI-LY-19 | DLBCL | GCB | |
| CARNAVAL | DLBCL | not specified | |
| Toledo | DLBCL | GCB | |
| RC-K8 | DLBCL | ABC | |
| SU-DHL-8 | DLBCL | GCB | |
| OCI-LY10 | DLBCL | ABC | |
| SU-DHL-16 | DLBCL | GCB | |
| U-2932 | DLBCL | ABC | |
| WILL-1 | DLBCL | not specified | |
| SU-DHL-4 | DLBCL | GCB | |
| Pfeiffer | DLBCL | GCB | |
| U-2904 | DLBCL | not specified | |
| WSU-DLCL | DLBCL | GCB | |
| HT | DLBCL | GCB | |
| RIVA | DLBCL | ABC | |

TABLE 6-continued

Hematological Cell Lines

| Cell Line | Tumor type | Tumor subtype | Culture conditions |
|---|---|---|---|
| ROS-50 | DLBCL | not specified | |
| GCBDB | DLBCL | GCB | |
| OCI-LY-7 | DLBCL | GCB | IMDM + 20% Human Plasma |
| OCI-LY-3 | DLBCL | ABC | |
| DOHH2 | FL | not specified | RPMI + 10% FBS, 1X NEAA, 2 |
| RL | FL | not specified | mM L-glutamine |
| Mino | MCL | not specified | RPMI1640 + 15% FBS + 2 mM L-glutamine + 10 mM Hepes + 1 mM sodium pyruvate + 4.5 g/L glucose |
| Rec-1 | MCL | not specified | RPMI + 10% FBS + 2 mM L-glutamine |
| EHEB | CLL | not specified | RPMI + 10% FBS, 1X NEAA, 2 |
| WA-C3-CD5+ | CLL | not specified | mM L-glutamine |
| WA-OSEL | CLL | not specified | |
| PGA1 | CLL | not specified | |
| HG3 | CLL | not specified | |
| I83-E95 | CLL | not specified | RPMI + 20% FBS, 1X NEAA, 2 |
| CII | CLL | not specified | mM L-glutamine |
| CI | CLL | not specified | |
| Mec2 | CLL | not specified | IMDM + 10% FBS |
| Mec1 | CLL | not specified | |
| SVSL/VL51 | MZL | SMZL | RPMI + 10% FBS, 1X NEAA, 2 mM L-glutamine |
| Daudi | BL | not specified | RPMI + 10% FBS + 2 mM L-glutamine |
| BL-41 | BL | not specified | RPMI1640 + 10% FBS + 1 mM sodium pyruvate + 50 µM 2-mercaptoethanol |
| MDS-L | MDS | not specified | RPMI + 10% FBS + 50 µM 2-mercaptoethanol + 50 U/mL + rhIL-3 |
| HNT-34 | AML | not specified | RPMI + 10% FBS + 2 mM L-glutamine |
| GDM-1 | AML | not specified | RPMI + 10% FBS |
| NCI-H929 | MM | not specified | RPMI + 10% FBS + GlutaMax |
| OPM-2 | MM | not specified | RPMI + 10% FBS |
| HuT-102 | TCL | not specified | |
| Karpas-299 | TCL | not specified | |
| JJN-3 | MM | PCL | |
| L-363 | MM | PCL | |
| SK-MM-1 | MM | PCL | 40% IMDM + 40% DMEM + 20% FBS |
| Karpas-231 | ALL | not specified | RPMI + 10% FBS |
| KOPN-8 | ALL | not specified | |
| L-428 | HL | not specified | |
| L-591 | HL | not specified | RPMI + 20% FBS |

ABC = activated B-cell like; FBS = fetal bovine serum; GCB = germinal center B-cell; IMDM = Iscove's Modified Dulbecco's medium; NEAA = non-essential amino acid; RPMI = RPMI1640.

The cell lines were plated in 384-well flat bottom plates and assessed with increasing concentrations of compound ranging from 0.00015 to 10 µM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the live-cell impermeant DNA dye, DRAQ7. Phosphatidylserine translocates from the inner layer to the outer layer of the cell membrane early in apoptosis and Annexin V binds to the exposed phosphatidylserine found on the surface of an apoptotic cell. The vital dye DRAQ7 is excluded by intact live cells and only stains cells that have died as a result of apoptosis or necrosis.

Flow cytometry data analysis was then performed using the Flow Jo_v10 software to determine the number of viable cells (Annexin V and DRAQ7 double negative staining cells) and percentage of apoptotic cells (Annexin V positive cells) for each condition. The live cell count for every concentration was normalized to the DMSO control (considered as 100%) to calculate the percentage of viable cells remaining after treatment and graphed using GraphPad Prism 7.03. The $IC_{50}$ (50% inhibitory concentration) and $E_{max}$ (maximum efficacy achieved) values were then calculated by performing nonlinear regression curve fitting using log(inhibitor) vs. normalized response—variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early" (Annexin V positive and DRAQ7 negative) and "late" apoptosis (Annexin V and DRAQ7 positive) cell gates relative to DMSO was graphed using GraphPad Prism 7.03. The AUC, $EC_{50}$ (concentration of compound that produces half-maximal apoptosis response) and $Y_{max}$ (maximal percentage of apoptosis achieved) values from apoptosis curves were calculated by performing area under curve analysis and nonlinear regression curve fitting using log(agonist) vs. normalized response—Variable slope analysis on GraphPad Prism 7.03.

Dose-response proliferation curves for the panel of hematological cell lines and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells). Tumor cells were exposed to serial dilutions (0.00015 to 10 µM) of Compound 1 or dimethyl sulfoxide (DMSO) control for 5 days. Viability and apoptosis for all cell lines was determined by Annexin V/7-aminoactinomycin D (7-AAD) flow cytometry. Compound 1 was found to have antiproliferative activity and/or apoptotic effects in almost all hematological cell lines tested, as shown in the following table.

TABLE 7

Antiproliferative Activity and Apoptotic Effect of Compound 1 in Hematological Cell Lines

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| ULA | 0.5518 | 0.00099 | 0.02523 | 995.3 | 0.00179 | 99.76 |
| SU-DHL-5 | 1.873 | 0.002389 | 0.1398 | 934.1 | 0.003603 | 95.23 |
| OCI-LY18 | 1.965 | 0.0009441 | 0.05973 | 965.2 | 0.002976 | 97.44 |
| TMD8 | 4.187 | 0.002459 | 0.245 | 963.3 | 0.006172 | 97.2 |
| SU-DHL-2 | 5.586 | 0.001263 | 0.2145 | 928.4 | 0.006242 | 95.98 |
| Farage | 10.16 | 0.002375 | 0.7936 | 728.7 | 0.03017 | 84.17 |
| SU-DHL-10 | 10.36 | 0.006101 | 0.6716 | 903 | 0.03942 | 92.27 |
| NU-DHL-1 | 12.37 | 0.001073 | 0.4919 | 981.8 | 0.001267 | 99.17 |
| VAL | 14.62 | 0.0005703 | 0.9632 | 936.7 | 0.0006045 | 95.68 |
| WILL-2 | 17.1 | 0.002359 | 0.03115 | 916.9 | 0.08971 | 99.43 |
| SU-DHL-6 | 19.94 | 0.03248 | 0.2469 | 920.7 | 0.1045 | 95.92 |
| KARPAS-422 | 19.97 | 0.01313 | 0.8721 | 911.9 | 0.0461 | 93.99 |
| NU-DUL-1 | 22.12 | 0.03527 | 0.0228 | 962.8 | 0.06304 | 99.84 |
| KARPAS-1106P | 22.22 | 0.01748 | 0.1698 | 885.2 | 0.09182 | 97.08 |
| OCI-LY1 | 22.77 | 0.006002 | 1.037 | 852.3 | 0.03338 | 90.09 |
| SU-DHL-1 | 31.14 | 0.0005495 | 2.485 | 690.1 | 0.001105 | 73.83 |
| WSU-DLCL2 | 36.7 | 0.01691 | 1.387 | 858.9 | 0.08473 | 92.1 |
| STR428 | 43.48 | 0.09471 | 1.227 | 905.9 | 0.1016 | 95.17 |
| U-2946 | 45.47 | 0.004604 | 0.4821 | 762.6 | 0.1922 | 93.34 |
| U-2940 | 70.43 | 0.006313 | 5.192 | 792.5 | 0.0314 | 82.19 |
| OCI-LY19 | 72.49 | 0.02944 | 3.228 | 706.2 | 0.2829 | 80.91 |
| CARNAVAL | 110.6 | 0.009122 | 7.134 | 708.7 | 0.1516 | 77.84 |
| Toledo | 112.3 | 0.002002 | 8.56 | 231.4 | 0.2231 | 27.5 |
| RC-K8 | 115.7 | 0.003371 | 10.06 | 349.2 | 0.07435 | 26.31 |
| SU-DHL-8 | 119.5 | 0.4857 | 2.081 | 363.2 | 0.6025 | 85.44 |
| OCI-LY10 | 125.3 | 0.01417 | 10.16 | 188.9 | 0.3202 | 22.31 |
| SU-DHL-16 | 149.7 | 0.1545 | 7.137 | 492.6 | 0.6619 | 60.79 |
| U-2932 | 163.7 | 0.03595 | 12.8 | 212.8 | 0.5669 | 25.81 |
| WILL-1 | 233.7 | 0.8166 | 4.216 | 549.4 | 2.515 | 79.51 |
| SU-DHL-4 | 296.2 | 0.2777 | 23.44 | 209 | 0.7823 | 25.33 |
| Pfeiffer | 313.5 | 0.04768 | 24.49 | 493.3 | 0.0136 | 51.82 |
| U-2904 | 334.1 | 0.2006 | 7.609 | 456.1 | 3.294 | 77.39 |
| WSU-DLCL | 341.9 | 0.142 | 27.83 | 565.1 | 0.01804 | 59.91 |
| HT | 396.7 | 0.3192 | 30.39 | 225.3 | 0.06622 | 25.16 |
| RIVA | 452.6 | 0.1135 | 36.65 | 242.8 | 0.01774 | 27.92 |
| ROS-50 | 762.1 | 10 | 65.57 | 87.92 | 0.3347 | 10.9 |
| U-2973 | 853.4 | 6.776 | 19.45 | 391.9 | 2.161 | 60.8 |
| DB | 941.4 | 10 | 89.46 | 80.31 | 0.06883 | 11.62 |
| OCI-LY7 | 48.18 | 0.006477 | 4.191 | 682.7 | 0.01627 | 71.18 |
| OCI-LY3 | 965.1 | 10 | 85.63 | 24.63 | 0.000263 | 4.493 |
| DOHH2 | 6.902 | 0.002801 | 0.2066 | 923.9 | 0.01753 | 95.1 |
| RL | 234.8 | 0.008755 | 21.55 | 115.9 | 0.1566 | 13.93 |
| Mino | 62.67 | 0.005782 | 5.638 | 968.2 | 0.002051 | 97.04 |
| Rec-1 | 281.8 | 0.03199 | 21.04 | 508.5 | 0.009258 | 57.27 |
| EHEB | 319.3 | 0.0303 | 28.68 | 65.03 | 0.5062 | 8.42 |
| WA-C3-CD5+ | 474.8 | 0.53 | 44.2 | 162.9 | 0.05244 | 17.47 |
| WA-OSEL | 616.1 | 10 | 54.42 | 69.39 | 0.112 | 7.38 |
| PGA1 | 736.7 | 10 | 69.21 | 48.94 | 0.1219 | 5.075 |
| HG3 | 676.2 | 10 | 59.58 | 131.5 | 0.1107 | 14.28 |
| I83-E95 | 259.2 | 0.01728 | 21.6 | 358.4 | 0.06111 | 40.69 |
| CII | 926.1 | 10 | 78.23 | 238.1 | 0.145 | 26.11 |
| CI | 603.9 | 9.701 | 53.58 | 123.2 | 0.02294 | 13.01 |
| Mec2 | 312.5 | 0.07552 | 25.55 | 339.8 | 0.01331 | 35.28 |
| Mec1 | 866.5 | 10 | 83.45 | 302.4 | 0.2097 | 36.61 |
| SVSL | 368.4 | 0.09517 | 34.07 | 340.2 | 0.002836 | 35.5 |
| Daudi | 196.4 | 0.0006 | 0 | 274 | 2.320 | 84.0 |
| BL-41 | 270.2 | 6.065 | 96.65 | 288.2 | 6.919 | 79.5 |
| MDS-L | 182.6 | 0.0513 | 146.7 | 425.4 | 1.557 | 100 |
| HNT-34 | 353 | 0.026 | 20.47 | 130.1 | 0.8756 | 44.33 |
| GDM-1 | 1455 | 6.8e−22 | 388.4 | 696.9 | 1.625e20 | 265 |
| NCI-H929 | 215.5 | 0.0007 | 6.1 | 16.86 | 11.27 | 7.00 |
| OPM-2 | 210.5 | 0.0003 | 6.65 | 212.6 | 1.316 | 63.00 |
| HuT-102 | 395.4 | 0.0065 | 36.34 | 42.75 | 23.36 | 18.50 |

TABLE 7-continued

Antiproliferative Activity and Apoptotic Effect of Compound 1 in Hematological Cell Lines

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| Karpas-299 | 283.7 | 0.012 | 8.43 | 14.51 | 167.6 | 8.0 |
| JJN-3 | 278.2 | 0.0004 | 21.6 | 57.97 | 5.14e22 | 26 |
| SK-MM-1 | 202.2 | 0.0008 | 3 | 90.99 | 86.36 | 44.5 |
| L-363 | 309.1 | 0.001 | 27.6 | 2.954 | 7.950 | 2 |
| Karpas-231 | 449.4 | 0.484 | 0 | 5.720 | 895.5 | 5.00 |
| KOPN-8 | 490.2 | 0.0418 | 38.3 | 14.95 | 726.5 | 5.00 |
| L-428 | 450.4 | 0.252 | 47.3 | 63.35 | 64.50 | 27.50 |
| L-591 | 334.2 | 0.0003 | 34.6 | 45.59 | 1.521 | 20.0 |

AUC = area under the curve; $IC_{50}$ = 50% inhibitory concentration (μM); $E_{max}$ = maximum efficacy eliminating tumor cells achieved expressed as the percentage of tumor cells remaining; $EC_{50}$ = compound concentration that produces half-maximal apoptosis response (μM); $Y_{max}$ = calculated percent of control at highest concentration of Compound 1.

6.3 Excipient Compatibility

Excipient Compatibility Study Design

The purpose of excipient compatibility study is to evaluate the impact of each excipient on Compound 1 stability, rank order excipient in each function category, and provide rational basis for excipient selection.

The following table listed the compositions of the excipient compatibility blends. The excipients covered many functionalities, including diluents, binders, disintegrant, glidant and lubricants. Considering the relatively high solubility of Compound 1, compared to the low dose (as low as 0.1 mg), dissolution might not be a critical issue, so surfactants were not included in the this excipient evaluation.

Due to low dose strength, segregation and content uniformity (CU) variation could be major process challenges. Granulation process (roller compaction or high shear wet granulation) might offer better options than direct blending to minimize segregation. Therefore, for each formulation blend, besides powder mix, compressed slug samples were made to mimic roller compression condition, and wet & dried samples were made to mimic wet granulation process condition.

The samples were evaluated for both chemical and chiral stability after subjecting the mixtures to open conditions at 5° C. (control), 50° C. (dry), and 50° C./75% RH (wet) for 2 weeks. Duplicate samples were prepared for each time point and condition.

TABLE 8

Compositions of Excipient Compatibility Blends

| Excipient Name | Trade Name | A w/w % | B w/w % | C w/w % | D w/w % | E w/w % | F w/w % | G w/w % | H w/w % | J w/w % | K w/w % | M w/w % | N w/w % | O w/w % |
|---|---|---|---|---|---|---|---|---|---|---|---|---|---|---|
| Compound 1 (HCl Salt) | | 0.2 | 0.2 | 0.2 | 0.2 | 0.2 | 0.2 | 0.2 | 0.2 | 0.3 | 0.3 | 0.8 | 0.8 | 0.2 |
| Mannitol | Pearlitol SD 200 | 69.8 | 73.8 | 69.8 | 65.8 | 69.8 | 65.8 | 69.2 | 65.2 | 99.7 | | | | 69.8 |
| Spray dried lactose monohydrate | Fast Flo 316 | | | | | | | | | | 99.7 | | | |
| Microcrystalline cellulose (MCC) | Avicel PH-105 | 25 | 25 | 25 | | | | 25 | | | | 99.2 | | |
| Pregelatinized starch | Starch 1500 | | | | 25 | 25 | 25 | | 25 | | | | 99.2 | 25 |
| Crospovidone | Kollidon CL | | | | 4 | 4 | 4 | | 4 | | | | | |
| Sodium stearyl fumarate (SSF) | PRUV | 5 | | | 5 | | | 5 | 5 | | | | | 5 |
| Magnesium stearate | HyQual | | 1 | | | 1 | | | | | | | | |
| Stearic acid | Kolliwax | | | 5 | | | 5 | | | | | | | |
| Silicon dioxide | Aerosil 200 | | | | | | | 0.6 | 0.6 | | | | | |
| Total | | 100 | 100 | 100 | 100 | 100 | 100 | 100 | 100 | 100 | 100 | 100 | 100 | 100 |

Excipient Compatibility Protocol

For each blend in the table, different forms (blend mix, slug and wet & dried mix) were used to mimic direct blend, roller compaction and wet granulation process conditions.

For each formulation blend, 120 mg of Compound 1 HCl salt (Form A) and corresponding excipients were accurately weighed. The blends were prepared by mixing for 20 minutes at 32 rpm on a Turbula mixer. For the slug sample, the blend was compressed in RRDI into slugs at 4.4KN for 100 ms. For wet mix sample, 20% water was added to the blend powder, magnetic stirring for 5 min, then put in the 50° C. oven for 1 hour.

All the samples were put on stability at 5° C., 50° C. ambient, 50° C./75% RH for 2 weeks for both chemical stability and chiral stability. The following two tables showed the chemical assay and chiral assay data, respectively.

Chemical Stability

TABLE 9

Chemical stability data for excipient compatibility study

| Formulation | Powder 2 Weeks | | | Slug 2 Weeks | | | Wet & Dry 2 Weeks | | |
|---|---|---|---|---|---|---|---|---|---|
| | Initial | 50° C. ambient | 50° C./ 75% RH | Initial | 50° C. ambient | 50° C./ 75% RH | Initial | 50° C. ambient | 50° C./ 75% RH |
| A-mcc/ssf | 98.1 | 97.3 | 95.8 | 98.3 | 97.1 | 95.2 | 97.5 | 90.6 | 87.6 |
| B-mcc/mg | 98.2 | 97.6 | 94.1 | 98.4 | 97.0 | 93.7 | 97.9 | NT | NT |
| C-mcc/sa | 98.3 | 96.4 | 97.8 | 98.5 | 97.5 | 97.1 | 98.2 | 94.9 | 94.8 |
| D-st/cr/ssf | 98.2 | 97.1 | 93.9 | 98.2 | 97.5 | 92.4 | 97.6 | 94.2 | 77.1 |
| E-st/cr/mg | 98.2 | 97.0 | 94.2 | 98.2 | 96.8 | 93.4 | 97.8 | 90.6 | 47.0 |
| F-st/cr/sa | 98.2 | 95.5 | 94.3 | 98.2 | 95.9 | 93.2 | 97.9 | 92.9 | 88.7 |
| G-mcc/ssf/sd | 98.5 | 97.6 | 96.3 | 98.5 | 96.9 | 95.6 | 97.9 | 91.3 | 77.4 |
| H-st/cr/ssf/sd | 98.3 | 97.4 | 95.9 | 98.2 | 97.2 | 95.8 | 97.7 | 90.0 | 68.3 |
| O-st/ssf | 98.3 | 97.4 | 96.3 | 98.6 | 97.8 | 96.0 | NT | NT | NT |
| J-mannitol | 98.5 | 97.9 | 98.3 | 98.6 | 97.2 | 98.5 | NT | NT | NT |
| K-lactose | 97.8 | 95.8 | 98.0 | N/A | N/A | N/A | NT | NT | NT |
| M-MCC | 98.3 | 97.9 | 98.0 | 98.3 | 97.7 | 97.5 | NT | NT | NT |
| N-starch | 98.4 | 97.7 | 97.8 | 98.4 | 97.5 | 98.2 | NT | NT | NT |

N/A = data not available
NT = not tested

Chiral Stability

TABLE 10

Chiral stability data for excipient compatibility study

| Formulation | Powder 2 Weeks | | | Slug 2 Weeks | | | Wet & Dry 2 Weeks | | |
|---|---|---|---|---|---|---|---|---|---|
| | Initial | 50° C. ambient | 50° C./ 75% RH | Initial | 50° C. ambient | 50° C./ 75% RH | Initial | 50° C. ambient | 50° C./ 75% RH |
| A-mcc/ssf | 98.5 | 98.5 | 91.9 | 98.7 | 98.2 | 92.3 | 95.7 | 86.0 | 86.0 |
| B-mcc/mg | 98.7 | 98.7 | 93.5 | 98.7 | 98.6 | 93.6 | 95.8 | NT | NT |
| C-mcc/sa | 98.7 | 97.8 | 94.9 | 98.8 | 98.6 | 86.9 | 98.6 | 93.5 | 74.6 |
| D-st/cr/ssf | 98.6 | 98.4 | 95.0 | 98.7 | 98.6 | 93.4 | 97.2 | 93.6 | 85.3 |
| E-st/cr/mg | 98.7 | 98.7 | 95.2 | 98.7 | 98.7 | 94.8 | 97.5 | 91.2 | 69.0 |
| F-st/cr/sa | 98.7 | 97.4 | 93.1 | 98.8 | 98.0 | 91.0 | 98.7 | 96.0 | 85.8 |
| G-mcc/ssf/sd | 98.6 | 98.6 | 93.2 | 98.6 | 98.2 | 93.3 | 96.7 | 81.4 | 65.0 |
| H-st/cr/ssf/sd | 98.7 | 98.6 | 94.8 | 98.7 | 98.4 | 93.9 | 97.2 | 87.0 | 73.0 |
| O-st/ssf | 98.8 | 98.4 | 93.5 | 98.8 | 98.5 | 92.5 | 95.8 | NT | NT |
| J-mannitol | 98.8 | 98.8 | 95.4 | 98.8 | 98.6 | 96.0 | 98.6 | NT | NT |
| K-lactose | 98.8 | 98.7 | 98.1 | N/A | N/A | N/A | 98.6 | NT | NT |
| M-MCC | 98.8 | 98.7 | 98.0 | 98.8 | 98.7 | 94.9 | 98.5 | NT | NT |
| N-starch | 98.8 | 98.7 | 97.3 | 98.8 | 98.7 | 97.5 | 98.8 | NT | NT |

N/A = data not available
NT = not tested

6.4 Prototype Formulation Stability

Prototype Formulation Design

Prototype capsule formulations were selected based on the results of excipient compatibility study, as shown in the following table.

For direct blending and roller compaction processes, since MCC and pregelatinized starch showed similar performance in stability in excipient compatibility, both were used in prototype formulations as binders; silicon dioxide was used as glidant; magnesium stearate and sodium stearyl fumarate were used as lubricants.

For wet granulation process, both MCC and pregelatinized starch were used, though the pregelatinized starch showed slightly better performance than MCC in excipient compatibility; silicon dioxide was not used; stearic acid, not magnesium stearate or sodium stearyl fumarate, was used as lubricant.

TABLE 11

Prototype formulation compositions

| Composition | Function | Direct Blending (DB) | | | Roller Compaction (RC) | | | Wet Granulation (WG) | | |
|---|---|---|---|---|---|---|---|---|---|---|
| | | Cap-1 % | Cap-2 % | Cap-3 % | Cap-4 % | Cap-5 % | Cap-6 % | Cap-7 % | Cap-8 % | Cap-9 % |
| Compound 1 (HCl Salt) | API | 0.14 | 0.14 | 0.14 | 0.14 | 0.14 | 0.14 | 0.14 | 0.14 | 0.14 |
| Mannitol | Diluent | 75.86 | 72.86 | 73.86 | 75.86 | 72.86 | 73.86 | 71.86 | 71.86 | |
| Microcrystalline cellulose (MCC) | Binder | | | 20 | | | 20 | | 20 | 84.86 |
| Pregelatinized starch | Binder | 20 | 20 | | 20 | 20 | | 20 | | |
| Crospovidone | Disintegrant | 3 | 3 | 3 | 3 | 3 | 3 | 3 | 3 | 10 |
| Silicon dioxide | Glidant | | 1 | | | 1 | | | | |
| Sodium stearyl fumarate (SSF) | Lubricant | | 3 | 3 | | 3 | 3 | | | |
| Magnesium stearate | Lubricant | 1 | | | 1 | | | | | |
| Stearic acid | Lubricant | | | | | | | 5 | 5 | 5 |
| Total % | | 100 | 100 | 100 | 100 | 100 | 100 | 100 | 100 | 100 |

Prototype Formulations Preparation

For direct blending formulations (Cap-1, Cap-2, Cap-3), excipients were passed through 30 mesh/595 μm screen, API was passed through 60 mesh/250 μm screen first; geometric dilution was used to improve mixing content uniformity—API was mixed with small portion of starch or MCC first at 15 rpm for 20 minutes, comil then mixed with the rest of the excipients (except magnesium stearate) at 15 rpm for 20 minutes, comil again, rinse the comil with mannitol, then final blend at 15 rpm for 10 minutes. If magnesium stearate was used as lubricant, magnesium stearate was added at the end for additional 3 minutes' blending at 15 rpm.

For roller compaction formulations (Cap-4, Cap-5, Cap-6), excipients were passed through 30 mesh/595 μm screen, API was passed through 60 mesh/250 μm screen first; geometric dilution was used to improve mixing content uniformity—API was mixed with small portion of starch or MCC first at 15 rpm for 20 minutes, comil (457 μm screen) then mixed with the rest of the intragranular excipients (except magnesium stearate) at 15 rpm for 20 minutes, comil (457 μm screen) again, rinse the comil with mannitol, then blend at 15 rpm for 10 minutes. If magnesium stearate was used as lubricant, intragranular magnesium stearate portion was added at the end for additional 3 minutes' blending at 15 rpm. The intragranular blend then was passed through a Gerteis Polygran roller compactor (serreated rolls, roll speed 2 rpm, roll gap 2.0 mm, roll force 4 kN/cm, screen opening 1.0 mm, granulator speed 50 rpm). Finally, extragranular lubricant was blended with the dry granules.

For wet granulation formulations (Cap-7, Cap-8, Cap-9), all excipients (except lubricant) and API were passed through 30 mesh/595 μm screen first, then were mixed in a Freund Vector high shear granulator bowl for 10 minutes at 300 rpm impeller speed and 3000 rpm chopper speed, then spray 20% water at 30 g/min with the same 300 rpm impeller speed and 3000 rpm chopper speed, followed by 1 minute of wet massing. The wet granules were passed through 5 mesh/4 mm screen, then dried in a Mini Glatt fluid bed dryer (inlet air temp 50° C., inlet air flow 50 CFM, product temp NMT 42° C.). The dried granules were passed through comil (610 μm screen), then blended with 30 mesh screened stearic acid (lubricant) for 10 minutes at 15 rpm.

All final blends were encapsulated in a Bosch GKF 702 encapsulator into Size 4 white opaque HPMC capsules with 75 mg fill weight.

The following table showed the initial testing results of the prototype formulation batches under different process conditions. For the same formulation compositions, batches using roller compaction process always had smaller AV values than batches using direct blending process (Cap-4 vs Cap-1, Cap-5 vs Cap-2, Cap-6 vs Cap-3); therefore, for better content uniformity, roller compaction process is preferred to direct blending process for Compound 1 HCl salt drug product manufacturing. Different processes had an impact on chemical stability. Total chemical degradation did not change much after roller compaction process, compared to direct blending; however, degradation increased after wet granulation process, which implied that wet granulation process might have a higher chemical stability risk level than roller compaction process. Chiral purity was not affected by different process conditions.

TABLE 12

Prototype formulation batches results

| Batch # | Process | AV* | Assay (% LC) | Total Chemical Degradation (%) | Chiral Purity (% S isomer) |
|---|---|---|---|---|---|
| Cap-4 | Roller compaction | 7.61 | 102.48 | 1.90 | 98.72 |
| Cap-1 | Direct blending | 10.64 | 97.41 | 1.70 | 98.74 |
| Cap-5 | Roller compaction | 7.42 | 98.29 | 1.75 | 98.71 |
| Cap-2 | Direct blending | 11.33 | 98.65 | 1.63 | 98.73 |
| Cap-6 | Roller compaction | 8.61 | 100.85 | 1.79 | 98.68 |
| Cap-3 | Direct blending | 9.16 | 96.74 | 1.58 | 98.73 |
| Cap-7 | Wet granulation | 16.51 | 101.46 | 2.45 | 98.72 |
| Cap-8 | Wet granulation | NT | 98.81 | 2.26 | 98.73 |
| Cap-9 | Wet granulation | NT | 81.70 | 2.68 | 98.66 |

*AV: acceptable value

Stability of Prototype Formulations

Capsules of each formulation were packaged into 50 100CC HDPE bottles, induction sealed, 10 counts per bottle; 35 bottles with 2 g desiccants, 15 bottles without desiccants. Stability was evaluated on the accelerated conditions (40° C./75% RH and 50° C./75% RH).

Figure 1A:
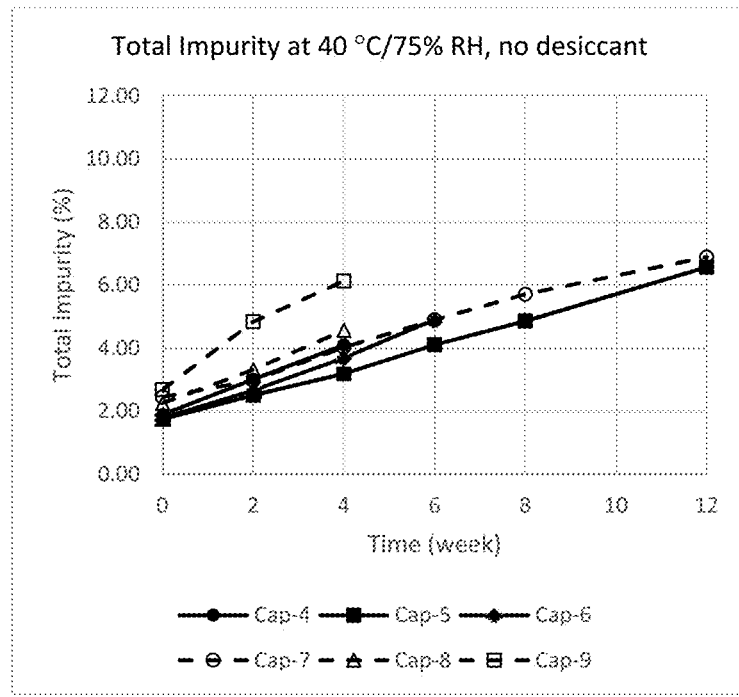
Figure 1B:
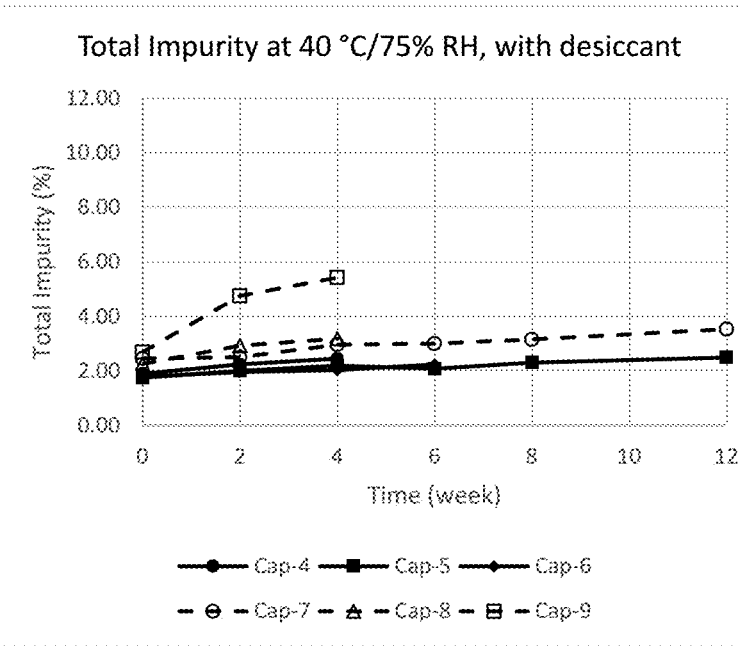
Figure 1C:
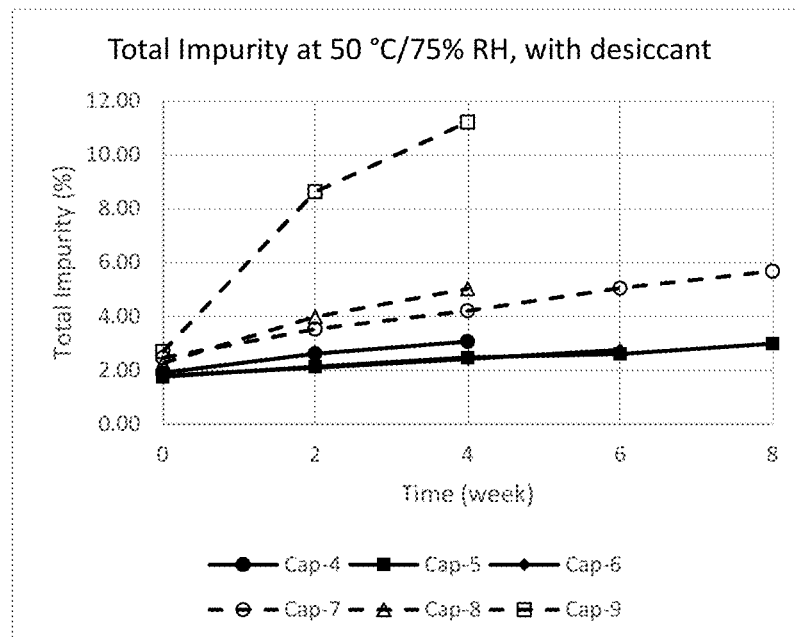

FIG. 1A, FIG. 1B, and FIG. 1C show chemical stability (total impurity) of prototype formulations for up to 12 weeks at 40° C./75% RH without desiccant, at 40° C./75% RH with desiccant, and at 50° C./75% RH with desiccant, respectively.

For the effect of desiccant vs no-desiccant on stability at 40° C./75% RH, formulations packaged with desiccant showed significantly slower impurity growth rate of API than the formulations packaged without desiccant, which implied that humidity control was important for drug product stability and hydrolysis was one of the main degradation pathways for Compound 1 HCl salt. Desiccant is needed to maintain Compound 1 HCl salt drug product shelf life.

For the three roller compaction formulations, at 40° C./75% RH with desiccant, Cap-5 and Cap-6 formulations showed similar total impurity growth rates, which was slower than that of Cap-4. At 50° C./75% RH with desiccant, the total impurity growth rates were faster than those at 40° C., but the ranking orders among the formulations did not change. The main composition difference between Cap-4 and Cap-5/Cap-6 was that magnesium stearate was used as lubricant in Cap-4, while sodium stearyl fumarate (SSF) was used in Cap-5/Cap-6 as lubricant. Therefore, SSF is preferred to magnesium stearate as lubricant in RC formulation. The binder used in Cap-5 was pregelatinized starch, while in Cap-6 it was microcrystalline cellulose. Cap-5 and Cap-6 had similar chemical stability profiles.

For the three wet granulation formulations, at 40° C./75% RH with desiccant, Cap-9 had a much faster impurity growth rate than Cap-7 and Cap-8. At 50° C./75% RH with desiccant, the impurity growth rates were faster than those at 40° C., but the ranking orders among the formulations did not change; Cap-8 had slightly faster impurity growth rate than Cap-7.

Cap-5 and Cap-7 had similar formulation compositions, but went through different granulation processes. Wet granulation formulation (Cap-7) had higher initial impurity level than roller compaction formulation (Cap-5), probably due to the process; while they had similar total impurity growth rates during stability.

Figure 2A:
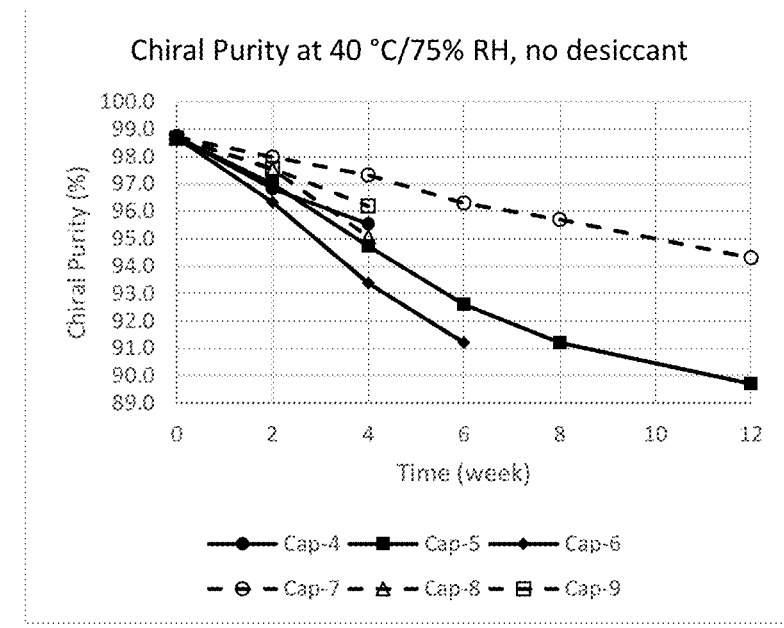
Figure 2B:
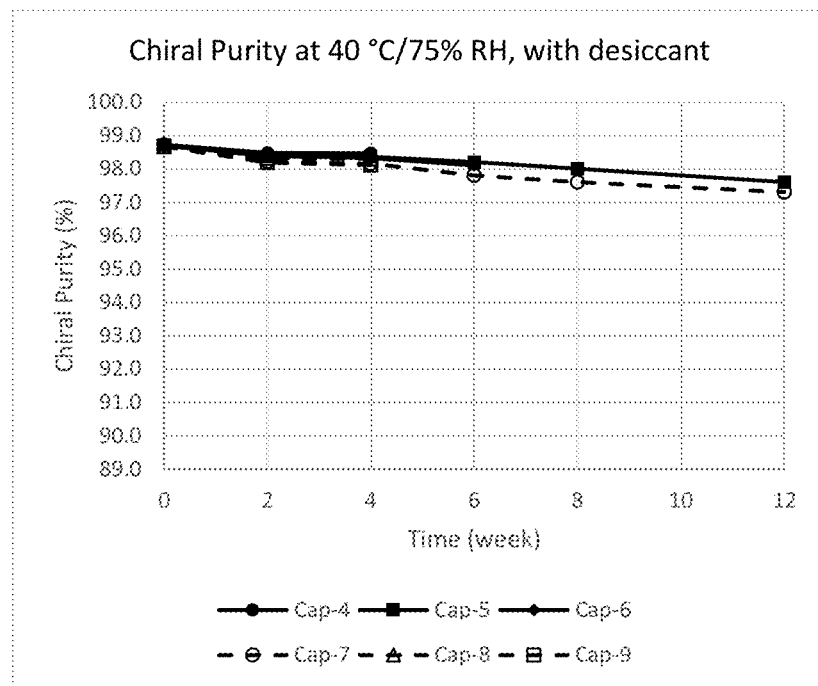
Figure 2C:
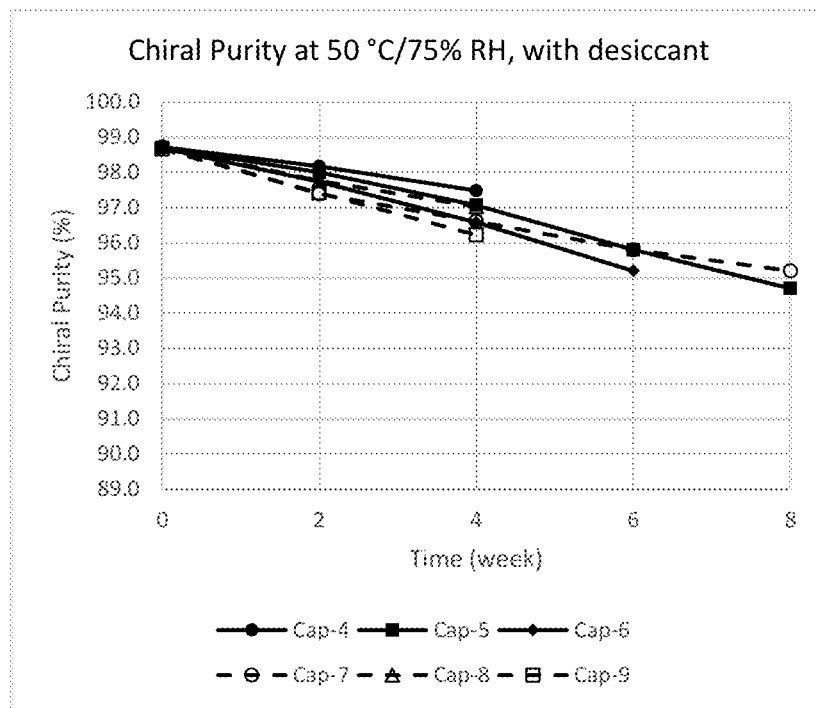

FIG. 2A, FIG. 2B, and FIG. 2C show chiral stability data of prototype formulations for up to 12 weeks at 40° C./75% RH without desiccant, at 40° C./75% RH with desiccant, and at 50° C./75% RH with desiccant, respectively.

For the effect of desiccant vs no-desiccant on stability at 40° C./75% RH, formulations packaged with desiccant showed significantly slower chiral isomerization rate of API than the formulations packaged without desiccant, which implied that humidity control was important for drug product chiral stability, desiccant is needed to maintain drug product shelf life.

For the roller compaction formulations, at 40° C./75% RH with desiccant, all three formulations showed slow chiral isomerization rates—about 1% decrease in chiral purity within 12 weeks. The order in chiral stability seemed to be Cap-4>Cap-5>Cap-6. At 50° C./75% RH with desiccant, the chiral isomerization rates were faster than those at 40° C., but the ranking orders among the formulations did not change. It seemed that chiral stability had less risk than chemical stability on drug product shelf life.

For the wet granulation formulations, at 40° C./75% RH with desiccant, three formulations also showed slow chiral isomerization rates—less than 1.5% decrease in chiral purity within 12 weeks. The order in chiral stability seemed to be Cap-8>Cap-7>Cap-9. At 50° C./75% RH with desiccant, the chiral isomerization rates were faster than those at 40° C., but the ranking orders among the formulations did not change.

Cap-5 and Cap-7 had similar formulation compositions, but went through different granulation processes. The two formulations started with the same chiral purity level; after 12 weeks, wet granulation formulation (Cap-7) had slightly less chiral purity level than roller compaction formulation (Cap-5). Cap-5 and Cap-7 were selected for further process development.

6.5 Process Evaluation Development (a) High-Shear Wet Granulation Process Evaluation and Development Intragranular/Extragranular Excipient Ratio The proposed clinical dose strength for Compound 1 HCl salt drug product was as low as 0.1 mg filled in 75 mg capsule, which was about 0.14% in drug load. Such an extremely low drug load presented challenges to process and content uniformity. High-shear wet granulation process not only could disperse the API well with high shear forces during blending, but could also form granules to prevent segregation during bulk storage and encapsulation. High-shear wet granulation process could be a good choice for low dose formulations with content uniformity concerns.

Figure 3:
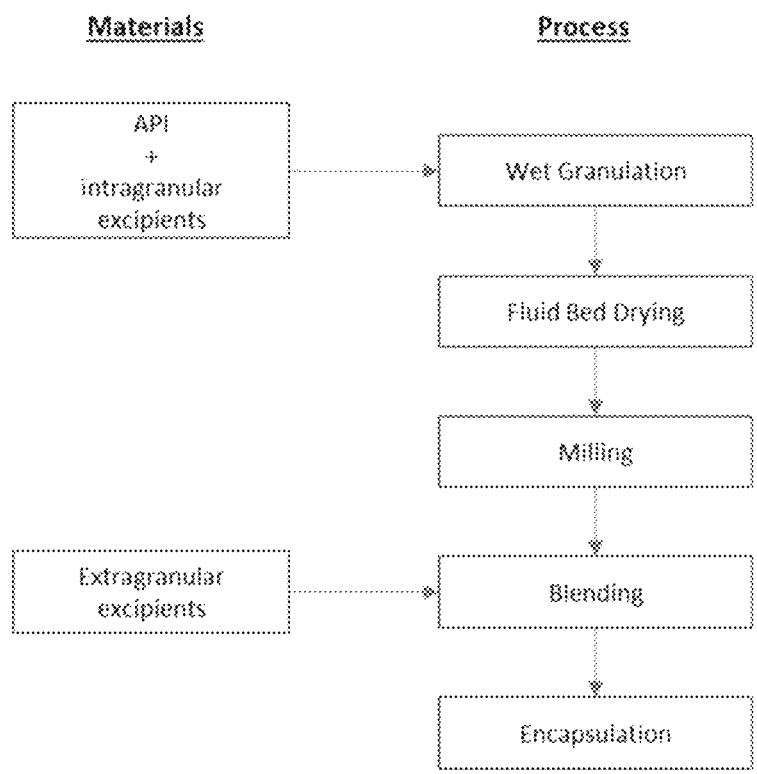

In order to improve the content uniformity of Cap-7 batch (CU % RSD 6.1%, AV 16.5), the wet granulation process was optimized. Since API drug amount was fixed, the intragranular/extragranular excipient ratio was reduced (from 95/5 to 23/77) to increase the intragranular blend drug load from 0.14% to 0.6%. FIG. 3 showed the process maps of wet granulation process. In the initial process, everything except for the lubricant was in the intragranular portion; while in the new process, API, pregelatinized starch and crospovidone were in the intragranular portion, mannitol and lubricant were in the extragranular portion.

Cap-10 batch was made using intragranular/extragranular excipient ratio of 23:77, while Cap-7 used intragranular/extragranular excipient ratio of 95:5. The process result of Cap-10 (CU % RSD 2.5%, AV 5.27) indicated that reducing intragranular/extragranular excipient ratio for wet granulation process could improve content uniformity. To confirm that conclusion, repeat batches were made—Cap-11 repeated the process of Cap-7, which used the initial high intragranular/extragranular excipient ratio of 95:5; while Cap-13 repeated the process of Cap-10. The process results in the following table showed that the batch repeatability was good—CU % RSD of Cap-7 and Cap-11 were comparable (6.1 vs 6.8), but much higher than those of Cap-10 and Cap-13 (2.5 vs 3.3). Therefore, it was confirmed that the new wet granulation process of lower intragranular/extragranular excipient ratio would improve content uniformity of low dose formulations.

Cap-13 was the repeat batch of Cap-10, using the lower intragranular/extragranular excipient ratio. Cap-10 had good CU data, but the CU of Cap-13 was not as good (3.3 vs 2.5). The following table listed the particle size distribution of Cap-10, Cap-13 and mannitol excipient (Pearlitol 200SD). The particle size of Cap-10 milled granules (D50 145 µm) matches the size of mannitol (D50 148 µm) well; however, the particle size of Cap-13 milled granules (D50 259 µm) was much larger than the size of mannitol (D50 148 µm), which might explain why the CU data of Cap-13 was not as good as Cap-10. The particle size of the final blends of Cap-10 and Cap-13 were similar because mannitol was the major component and dominated the average particle size of the final blend, not the milled granules.

In another repeat batch (Cap-14), the particle size of milled granules was monitored and controlled before mixing with mannitol and lubricant. The milled granule size (D50 139 µm) matched that of Cap-10 milled granules and mannitol, which might explain why the CU % RSD of Cap-14 (2.0) was as good as that of Cap-10 (2.5).

TABLE 13

Summary process results of high-shear wet granulation development batches

| Lot Number | Strength | API Screen | Excipient screen | Assay (%) | CU % RSD | AV |
|---|---|---|---|---|---|---|
| Cap-7 | 0.1 mg | 30 mesh | 30 mesh | 101.46 | 6.1 | 16.51 |
| Cap-10 | 0.1 mg | 30 mesh | 30 mesh | 101.7 | 2.5 | 5.27 |
| Cap-11 | 0.1 mg | 30 mesh | 30 mesh | 109.4 | 6.8 | 21.5 |
| Cap-12 | 0.1 mg | 60 mesh | 30 mesh | 99.1 | 3.5 | 8.5 |
| Cap-13 | 0.1 mg | 30 mesh | 30 mesh | 96.2 | 3.3 | 10.3 |
| Cap-14 | 0.1 mg | 60 mesh | 30 mesh | 91 | 2.0 | 11.5 |

API Screen Pore Size

API particle size could also affect content uniformity, because smaller API particles could be better dispersed. Compound 1 HCl salt API crystals tend to agglomerate; although the high shear blending force could break up agglomerates, for low dose formulation, it's not as efficient as passing through mesh screens. For high intragranular/extragranular excipient ratio process, batch Cap-12 passed API through 60 mesh (250 µm) screen, compared with Cap-7 and Cap-11 using 30 mesh (595 µm) screen. As the result, CU % RSD was greatly reduced from 6.1% of Cap-7 to 3.5% of Cap-12. The trend was also true for the new wet granulation process of lower intragranular/extragranular excipient ratio—CU % RSD was reduced to 2.0% in Cap-14 from 2.5% of Cap-10 after changing the API screen mesh number from 30 to 60. Therefore, passing API through smaller screen pore size could improve batch content uniformity.

Milled Granule Particle Size Match

In the low intragranular/extragranular excipient ratio (23/77) wet granulation process, the API was mixed with starch, crospovidone and water, formed wet granules and then dried and milled through comil; the milled granules were then mixed with mannitol and lubricant to form the final blend. Since mannitol powder accounted for the majority (~72% w/w) of the final blend, it's important for the particle size of the milled granules to match that of mannitol to minimize segregation.

TABLE 14

Particle size distributions of wet granulation batches and main excipients

| Sample Name | D (10) (µm) | D (50) (µm) | D (90) (µm) |
|---|---|---|---|
| Cap-10 milled granules | 38 | 145 | 448 |
| Cap-10 final blend | 73 | 158 | 323 |
| Cap-13 milled granules | 76 | 259 | 573 |
| Cap-13 final blend | 62 | 150 | 301 |
| Cap-14 milled granules | 33 | 139 | 440 |
| Cap-14 final blend | NT | NT | NT |
| Mannitol (Pearlitol 200SD) | 85 | 148 | 237 |
| Pregelatinized starch (Starch 1500) | 18 | 88 | 183 |

NT: not tested

SEM images (not shown herein) were taken from excipients, milled granules and final blends to have a better understanding on the size and surface morphology of the particles. The SEM images of pregelatinized starch (Starch 1500) and mannitol (Pearlitol 200SD) showed that most of the pregelatinized starch particles were smaller than mannitol particles. The SEM images of Cap-10 milled granules showed that the milled granule particles were mostly aggregates of starch particles, and size of the granules were similar to that of mannitol. The SEM images of Cap-10 final blend showed that it consisted of mannitol particles.

In summary, for high-shear wet granulation process, the content uniformity of low dose formulation can be improved, when reducing the intragranular/extragranular excipient ratio, passing API through smaller pore size screen and matching the size of milled granules to that of mannitol.

(b) Roller Compaction Process Evaluation and Development

Intragranular/Extragranular Excipient Ratio

The proposed clinical dose strength for Compound 1 HCl salt drug product was as low as 0.1 mg filled in 75 mg capsule, which was about 0.14% in drug load. Such an extremely low drug load presented challenges to process and content uniformity. Roller compaction process itself could not help API dispersed evenly, but could help prevent segregation afterwards; in order to achieve good content uniformity, the API should be well dispersed before the roller compaction step.

Figure 4:
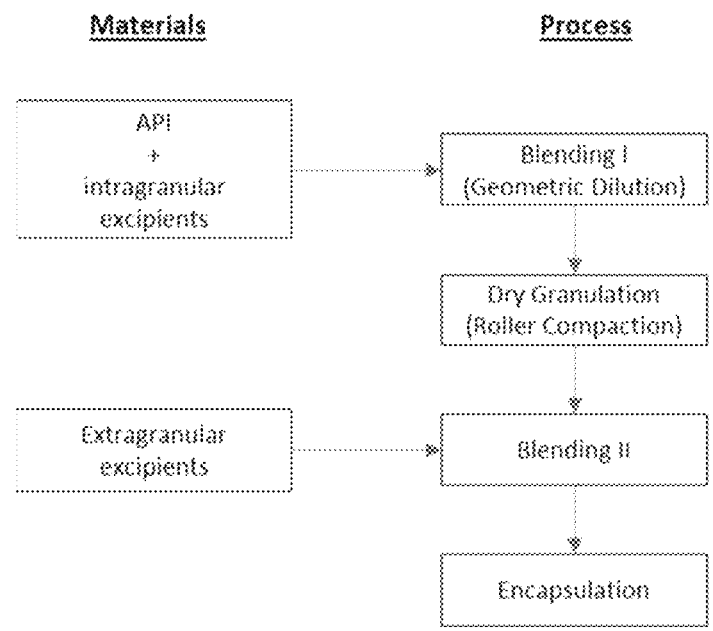

Geometric dilution was utilized in Cap-5 batch to improve blending uniformity, and got acceptable content uniformity result (3.1% RSD, AV 7.4). To further improve content uniformity, increasing the intragranular drug load before roller compaction was tested. Since API drug amount was fixed, the intragranular/extragranular excipient ratio needed to be reduced (from 98/2 to 14/86) to increase the intragranular blend drug load from 0.14% to 1%. FIG. 4 showed the process maps of RC process.

While Cap-5 used the initial roller compaction process of intragranular/extragranular excipient ratio of 98:2, Cap-15 batch was made using the new roller compaction process of intragranular/extragranular excipient ratio of 14:86. Since starch alone could not be successfully roller compacted, in Cap-15, the excipient ratios within the intragranular portion was kept similar to the excipient ratios within the extragranular portion.

In Cap-5 batch, API was passed through 60 mesh (250 μm) screen before blending; however, since it was uncommon to use 60 mesh screen for scale-up batch manufacturing, 30 mesh (595 μm) screen was used in Cap-15 batch for both API and excipients. There were no other process changes between Cap-15 and Cap-5.

The following table listed the summary process results of roller compaction development batches. The CU % RSD of Cap-15 was higher than that of Cap-5 (9.0 vs 3.1). Even a repeat batch (Cap-16) with extra blending and compiling steps did not change much on the content uniformity (CU % RSD of 8.6). Unlike wet granulation process, the new approach with lower intragranular/extragranular excipient ratio (14:86) did not improve content uniformity of low dose formulations in roller compaction process.

ents when the extragranular excipients accounted for most of the final blend. Additional work was needed to find out the proper process conditions to control the particle size of milled granules to match the particle size of extragranular excipients for the low intragranular/extragranular excipient ratio process. However, since the conventional high intragranular/extragranular excipient ratio process could already achieve acceptable CU, more work on new process was not warranted.

TABLE 16

Particle size distributions of roller compaction batches

| Sample Name | D (10) (μm) | D (50) (μm) | D (90) (μm) |
|---|---|---|---|
| Cap-5 final blend | 8 | 110 | 595 |
| Cap-15 milled granules | 16 | 145 | 568 |
| Cap-15 final blend | 18 | 126 | 238 |
| Cap-16 milled granules | 16 | 154 | 659 |
| Cap-16 final blend | 18 | 131 | 279 |
| Cap-17 milled granules | 15 | 165 | 786 |
| Cap-17 final blend | 14 | 146 | 780 |
| Cap-18 milled granules | 31 | 253 | 864 |
| Cap-18 final blend | 17 | 173 | 832 |

API Screen Pore Size

API particle size could also affect content uniformity, because smaller API particles tend be better dispersed. Compound 1 HCl salt API crystals tend to agglomerate, and the blending process was too gentle to break down large agglomerates, so passing API powder through mesh screen before blending was an effective way to break down large agglomerates.

For initial high intragranular/extragranular excipient ratio process, batch Cap-5 passed API through 60 mesh (250 μm) screen and got acceptable CU % RSD (3.1%); however, when Cap-17 increased the API screen pore size to 30 mesh (595 μm), CU % RSD increased to 5.8%. When Cap-18 reduced the API screen pore size back to 60 mesh (250 μm), the CU % RSD went back to 2.9%. Therefore, passing API through smaller screen pore size could improve roller compaction batch content uniformity.

In summary, for roller compaction process, passing API through 60 mesh, not 30 mesh, screen was important for the content uniformity of low dose formulation.

6.6 Evaluation and Manufacture of Formulations

Cap-5 and Cap-7 had similar formulation compositions, but went through different granulation processes. Wet granu-

TABLE 15

Summary process results of roller compaction development batches

| Lot Number | Strength | API Screen | Excipient screen | Assay (% LC) | CU % RSD | AV |
|---|---|---|---|---|---|---|
| Cap-5 | 0.1 mg | 60 mesh | 30 mesh | 98.29 | 3.1 | 7.42 |
| Cap-15 | 0.1 mg | 30 mesh | 30 mesh | 103.4 | 9.0 | 19.9 |
| Cap-16 | 0.1 mg | 30 mesh | 30 mesh | 95.5 | 8.6 | 20.2 |
| Cap-17 | 0.1 mg | 30 mesh | 30 mesh | 103.8 | 5.8 | 13.9 |
| Cap-18 | 0.1 mg | 60 mesh | 30 mesh | 92.4 | 2.9 | 11.9 |

Particle size analysis was carried out for milled granules and final blends of roller compaction batches, and the results are listed in the following table. For Cap-15 and Cap-16 batches, the D (50) values of milled granules and final blend were similar; however, there were huge differences in D (90) values between milled granules and final blend, which indicated that milled granules had too many large particles that could not be blended well with the extragranular excipilation formulation (Cap-7) had 0.7% more initial total impurity level than roller compaction formulation (Cap-5), probably because the wetting and drying of wet granulation process induced more chemical degradations; while the total impurity growth rates of the two batches were similar during stability study. Both formulations required desiccant to maintain suitable shelf life. Overall, wet granulation process had higher risk than roller compaction process in chemical stability. For chiral purity, the two formulations were similar.

Manufacturability was evaluated in content uniformity and assay value. Based on the process development data, although wet granulation batches had better content uniformity (CU % RSD) than roller compaction process, the content uniformity of the roller compaction batches were still acceptable. Roller compaction had less risk for API loss (assay value) than wet granulation process, because the roller compaction process was much simpler.

Figure 5:
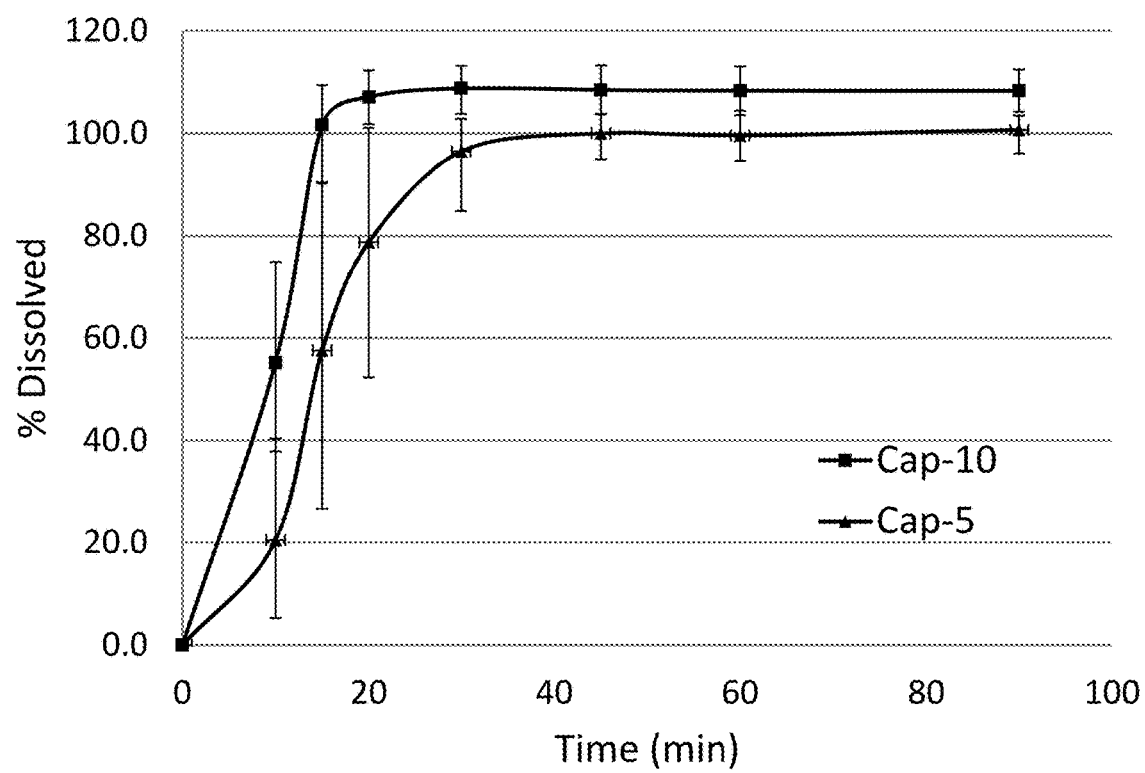
FIG. 5 shows dissolution Profiles of roller compaction batch (Cap-5) and high-shear wet granulation batch (Cap-10).

Since the solubility of Compound 1 HCl salt API was relatively high, compared to the proposed dose levels, the risk on drug product dissolution was low. FIG. 5 showed the performance (dissolution profile) of the formulations of two granulation processes. Although wet granulation batch (Cap-10) had faster dissolution rate, roller compaction batch (Cap-5) still had good enough dissolution rate.

Roller compaction and Cap-5 formulation were selected for further evaluation. The following three tables listed the formulation compositions for different dose strengths. Since desiccant was required, hydroxypropylmethyl cellulose (HPMC), not gelatin, was selected as capsule shell material, because gelatin capsules would crack in the presence of desiccant during storage.

TABLE 17

Composition of Capsules, 0.1 mg strength

| Components | Function | Trade Name | Quality standard | Amount per Capsule (mg) | (%) |
|---|---|---|---|---|---|
| Compound 1 HCl, Salt | Active | | | 0.107 | 0.142% |
| Mannitol | Filler | Pearlitol 200 SD | USP/Ph. Eur./JP | 54.64 | 72.86% |
| Pregelatinized Starch | Binder | Starch 1500 | NF/Ph. Eur. | 15.00 | 20.00% |
| Crospovidone | Disintegrant | Kollidon CL | NF/Ph. Eur./JP | 2.25 | 3.00% |
| Silicon Dioxide | Glidant | Aerosil 200 | NF/Ph. Eur./JP | 0.75 | 1.00% |
| Sodium Stearyl Fumarate | Lubricant | PRUV | NF/Ph. Eur./JP | 2.25 | 3.00% |
| | Capsule Fill Weight | | | 75.0 | |
| HPMC Capsule, Size 4, Opaque White | Capsule Shell | Vcaps Plus | USP/NF/EP/JP | 38.0 | |
| | Total Capsule Weight | | | 113.0 [1] | 100.0% |

[1] Approximate filled capsule weight based on capsule weight of 38.0 mg.

TABLE 18

Composition of Capsules, 0.5 mg strength

| Components | Function | Trade Name | Quality standard | Amount per Capsule (mg) | (%) |
|---|---|---|---|---|---|
| Compound 1 HCl, Salt | Active | | | 0.534 | 0.712% |
| Mannitol | Filler | Pearlitol 200 SD | USP/Ph. Eur./JP | 54.22 | 72.29% |
| Pregelatinized Starch | Binder | Starch 1500 | NF/Ph. Eur. | 15.00 | 20.00% |
| Crospovidone | Disintegrant | Kollidon CL | NF/Ph. Eur./JP | 2.25 | 3.00% |
| Silicon Dioxide | Glidant | Aerosil 200 | NF/Ph. Eur./JP | 0.75 | 1.00% |
| Sodium Stearyl Fumarate | Lubricant | PRUV | NF/Ph. Eur./JP | 2.25 | 3.00% |
| | Capsule Fill Weight | | | 75.0 | |
| HPMC Capsule, Size 4, Swedish Orange | Capsule Shell | Vcaps Plus | USP/NF/EP/JP | 38.0 | |
| | Total Capsule Weight | | | 113.0 [1] | 100.0% |

[1] Approximate filled capsule weight based on capsule weight of 38.0 mg.

TABLE 19

| Composition of Capsules, 1.5 mg strength | | | | | |
|---|---|---|---|---|---|
| | | | | Amount per Capsule | |
| Components | Function | Trade Name | Quality standard | (mg) | (%) |
| Compound 1 HCl, Salt | Active | | | 1.602 | 0.712% |
| Mannitol | Filler | Pearlitol 200 SD | USP/Ph. Eur./JP | 162.65 | 72.29% |
| Pregelatinized Starch | Binder | Starch 1500 | NF/Ph. Eur. | 45.00 | 20.00% |
| Crospovidone | Disintegrant | Kollidon CL | NF/Ph. Eur./JP | 6.75 | 3.00% |
| Silicon Dioxide | Glidant | Aerosil 200 | NF/Ph. Eur./JP | 2.25 | 1.00% |
| Sodium Stearyl Fumarate | Lubricant | PRUV | NF/Ph. Eur./JP | 6.75 | 3.00% |
| | Capsule Fill Weight | | | 225.0 | |
| HPMC Capsule, Size 1, Swedish Orange | Capsule Shell | Vcaps Plus | USP/NF/EP/JP | 75.0 | |
| | Total Capsule Weight | | | 300.0 [1] | 100.0% |

[1] Approximate filled capsule weight based on capsule weight of 75.0 mg.

Figure 6:
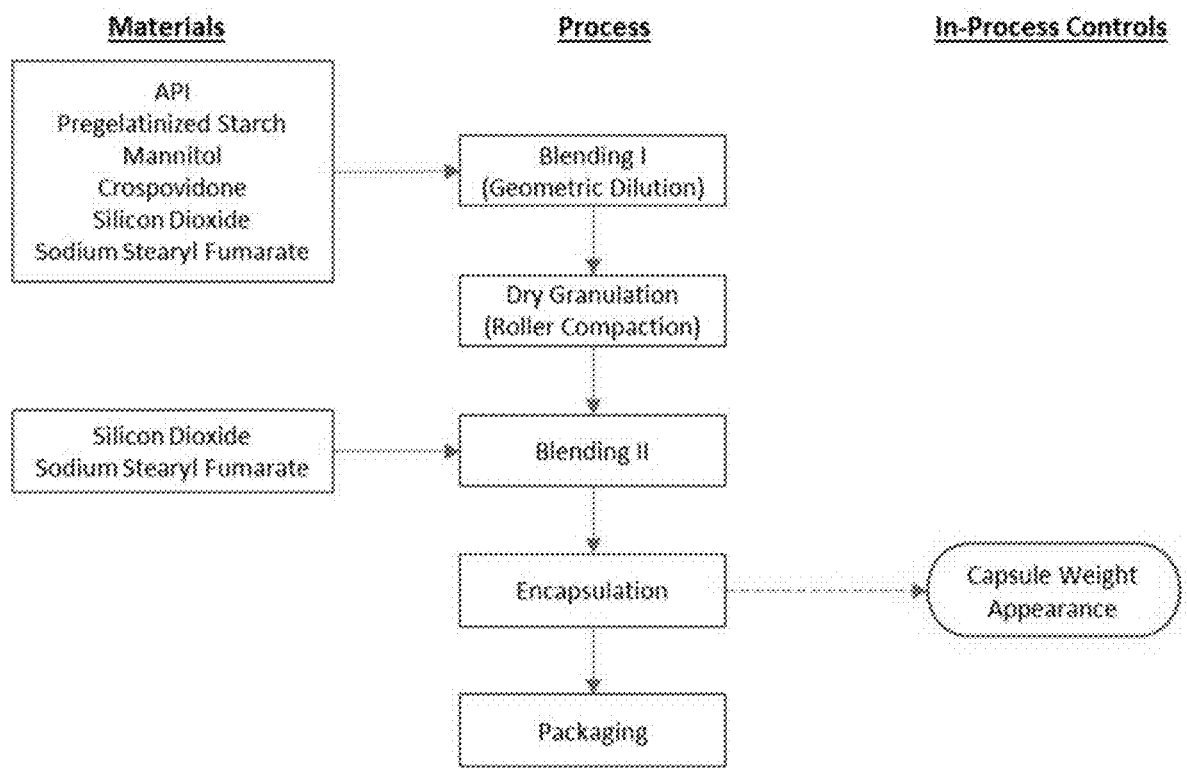
FIG. 6 shows process map of roller compaction process for batches of Cap-5 formulations.

FIG. 6 showed the process map of roller compaction process for the above batches. A description of the manufacturing process for Compound 1 HCl salt capsules is provided below: (i) Compound 1 HCl salt is pre-blended with a small portion of the pregelatinized starch, then blended with the remaining intragranular excipients (pregelatinized starch, mannitol, crospovidone, silicon dioxide, sodium stearyl fumarate); (ii) the intragranular blend is passed through a roller compactor; (iii) the extragranular silicon dioxide and sodium stearyl fumarate are passed through a screen and added to the granules and blended; and (iv) the appropriate size capsule is filled to the specified weight.

Three batches of 3 kg scale (Cap-19, Cap-20, Cap-21, 0.1 mg, 0.5 mg, and 1.5 mg dose strength respectively) were manufactured and packaged. The following table listed the results of the stability batches. The capsules were packaged in 100CC opaque high-density polyethylene (HDPE) bottles fitted with induction seal and with tamper evident child resistant polypropylene caps. Each bottle contained 21 capsules and a 2 g desiccant.

TABLE 20

| Batches results | | | |
|---|---|---|---|
| Lot # | Dose strength | Assay (% LC) | CU % RSD | AV |
| Cap-19 | 0.1 mg | 96.1% | 2.43% | 8.4 |
| Cap-20 | 0.5 mg | 97.2% | 1.61% | 3.8 |
| Cap-21 | 1.5 mg | 96.2% | 1.89% | 5.5 |

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A pharmaceutical composition comprising Compound 1:

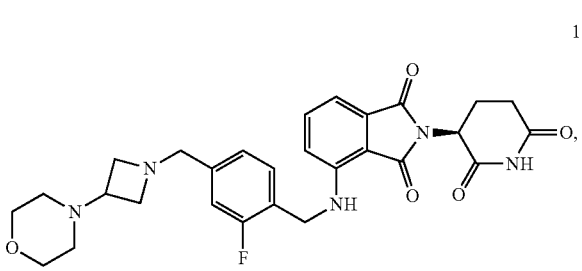 [SMILES: O=C1CC[C@H](N2C(=O)c3cccc(NCc4ccc(CN5CC(N6CCOCC6)C5)cc4F)c3C2=O)C(=O)N1]

or an enantiomer, mixture of enantiomers, tautomer, or pharmaceutically acceptable salt thereof, and a carrier or diluent, wherein the carrier or diluent is a mixture of mannitol and starch, a mixture of mannitol and cellulose, or cellulose.

2. The pharmaceutical composition of claim 1, wherein the carrier or diluent is a mixture of mannitol and starch.

3. The pharmaceutical composition of claim 2, comprising: (i) Compound 1, or an enantiomer, mixture of enantiomers, tautomer, or pharmaceutically acceptable salt thereof, at an amount of from about 0.05 to about 2% w/w; (ii) a mixture of mannitol and starch at an amount of from about 85 to about 99.7% w/w; (iii) a disintegrant at an amount of from about 0 to about 6% w/w; (iv) a glidant at an amount of from about 0 to about 2% w/w; and a lubricant at an amount of from about 0 to about 10% w/w.

4. The pharmaceutical composition of claim 3, wherein Compound 1, or an enantiomer, mixture of enantiomers, tautomer, or pharmaceutically acceptable salt thereof, is a hydrochloride salt of Compound 1.

5. The pharmaceutical composition of claim 4, wherein the hydrochloride salt of Compound 1 is a crystalline hydrochloride salt of Compound 1.

6. The pharmaceutical composition of claim 4, wherein the hydrochloride salt of Compound 1 is characterized by an XRPD pattern comprising peaks at approximately 15.1, 16.3, and 20.7° 2θ.

7. The pharmaceutical composition of claim 3, wherein the amount of Compound 1, or an enantiomer, mixture of enantiomers, tautomer, or pharmaceutically acceptable salt thereof, is from about 0.1 to about 1% w/w.

8. The pharmaceutical composition of claim 7, wherein the amount of Compound 1, or an enantiomer, mixture of enantiomers, tautomer, or pharmaceutically acceptable salt thereof, is from about 0.14 to about 0.71% w/w.

9. The pharmaceutical composition of claim 3, wherein the starch is pregelatinized starch.

10. The pharmaceutical composition of claim 3, wherein the amount of mannitol is from about 67 to about 77.7% w/w, and the amount of the starch is from about 18 to about 22% w/w.

11. The pharmaceutical composition of claim 3, wherein the amount of the mixture of mannitol and starch is from about 90 to about 95% w/w.

12. The pharmaceutical composition of claim 11, wherein the amount of the mannitol is from about 71 to about 74% w/w, and the amount of the starch is from about 19 to about 21% w/w.

13. The pharmaceutical composition of claim 3, wherein the amount of the mixture of mannitol and starch is from about 91.5 to about 93% w/w.

14. The pharmaceutical composition of claim 13, wherein the amount of the mannitol is from about 71.5 to about 73% w/w, and the amount of the starch is about 20% w/w.

15. The pharmaceutical composition of claim 3, wherein the weight ratio of the starch to the mannitol is from about 1:3 to about 1:4.

16. The pharmaceutical composition of claim 15, wherein the weight ratio of the starch to the mannitol is about 1:3.6.

17. The pharmaceutical composition of claim 3, wherein the disintegrant is crospovidone.

18. The pharmaceutical composition of claim 3, wherein the amount of the disintegrant is from about 1 to about 5% w/w.

19. The pharmaceutical composition of claim 18, wherein the amount of the disintegrant is about 3% w/w.

20. The pharmaceutical composition of claim 3, wherein the glidant is silicon dioxide.

21. The pharmaceutical composition of claim 3, wherein the amount of the glidant is from about 0.5 to about 1.5% w/w.

22. The pharmaceutical composition of claim 21, wherein the amount of the glidant is about 1% w/w.

23. The pharmaceutical composition of claim 3, wherein the lubricant is sodium stearyl fumarate, stearic acid, or magnesium stearate.

24. The pharmaceutical composition of claim 3, wherein the amount of the lubricant is from about 1.5 to about 7.5% w/w.

25. The pharmaceutical composition of claim 24, wherein the amount of the lubricant is from about 3 to about 5% w/w.

26. The pharmaceutical composition of claim 3, comprising: (i) a hydrochloride salt of Compound 1 at an amount of about 0.14% w/w; (ii) mannitol at an amount of about 72.86% w/w and pregelatinized starch at an amount of about 20% w/w; (iii) crospovidone at an amount of about 3% w/w; (iv) silicon dioxide at an amount of about 1% w/w; and (v) sodium stearyl fumarate at an amount of about 3% w/w.

27. The pharmaceutical composition of claim 26, having a total weight of about 75 mg.

28. The pharmaceutical composition of claim 27, which is contained in a size 4 capsule.

29. The pharmaceutical composition of claim 3, comprising: (i) a hydrochloride salt of Compound 1 at an amount of about 0.71% w/w; (ii) mannitol at an amount of about 72.29% w/w and pregelatinized starch at an amount of about 20% w/w; (iii) crospovidone at an amount of about 3% w/w; (iv) silicon dioxide at an amount of about 1% w/w; and (v) sodium stearyl fumarate at an amount of about 3% w/w.

30. The pharmaceutical composition of claim 29, having a total weight of about 75 mg.

31. The pharmaceutical composition of claim 30, which is contained in a size 4 capsule.

32. The pharmaceutical composition of claim 29, having a total weight of about 225 mg.

33. The pharmaceutical composition of claim 32, which is contained in a size 1 capsule.

34. The pharmaceutical composition of claim 3, comprising: (i) a hydrochloride salt of Compound 1 at an amount of about 0.14% w/w; (ii) mannitol at an amount of about 71.86% w/w and pregelatinized starch at an amount of about 20% w/w; (iii) crospovidone at an amount of about 3% w/w; and (iv) stearic acid at an amount of about 5% w/w.

35. The pharmaceutical composition of claim 3, comprising: (i) a hydrochloride salt of Compound 1 at an amount of about 0.14% w/w; (ii) mannitol at an amount of about 75.86% w/w and pregelatinized starch at an amount of about 20% w/w; (iii) crospovidone at an amount of about 3% w/w; and (iv) magnesium stearate at an amount of about 1% w/w.

36. The pharmaceutical composition of claim 1, wherein the carrier or diluent is a mixture of mannitol and cellulose.

37. The pharmaceutical composition of claim 36, comprising: (i) Compound 1, or an enantiomer, mixture of enantiomers, tautomer, or pharmaceutically acceptable salt thereof, at an amount of from about 0.05 to about 2% w/w; (ii) a mixture of mannitol and cellulose at an amount of from about 85 to about 99.7% w/w; (iii) a disintegrant at an amount of from about 0 to about 6% w/w; and (iv) a lubricant at an amount of from about 0 to about 10% w/w.

38. The pharmaceutical composition of claim 37, comprising: (i) a hydrochloride salt of Compound 1 at an amount of about 0.14% w/w; (ii) mannitol at an amount of about 73.86% w/w and microcrystalline cellulose at an amount of about 20% w/w; (iii) crospovidone at an amount of about 3% w/w; and (iv) sodium stearyl fumarate at an amount of about 3% w/w.

39. The pharmaceutical composition of claim 37, comprising: (i) a hydrochloride salt of Compound 1 at an amount of about 0.14% w/w; (ii) mannitol at an amount of about 71.86% w/w and microcrystalline cellulose at an amount of about 20% w/w; (iii) crospovidone at an amount of about 3% w/w; and (iv) stearic acid at an amount of about 5% w/w.

40. The pharmaceutical composition of claim 1, wherein the carrier or diluent is cellulose.

41. The pharmaceutical composition of claim 40, comprising: (i) Compound 1, or an enantiomer, mixture of enantiomers, tautomer, or pharmaceutically acceptable salt thereof, at an amount of from about 0.05 to about 2% w/w; (ii) cellulose at an amount of from about 75 to about 95% w/w; (iii) a disintegrant at an amount of from about 0 to about 20% w/w; and (iv) a lubricant at an amount of from about 0 to about 10% w/w.

42. The pharmaceutical composition of claim 41, comprising: (i) a hydrochloride salt of Compound 1 at an amount of about 0.14% w/w; (ii) microcrystalline cellulose at an amount of about 84.86% w/w; (iii) crospovidone at an amount of about 10% w/w; and (iv) stearic acid at an amount of about 5% w/w.

* * * * *